US006689759B1

(12) United States Patent
Jacob et al.

(10) Patent No.: US 6,689,759 B1
(45) Date of Patent: Feb. 10, 2004

(54) METHODS OF TREATING HEPATITIS VIRUS INFECTIONS WITH N-SUBSTITUTED-1,5-DIDEOXY-1,5-IMINO-D-GLUCITOL COMPOUNDS IN COMBINATION THERAPY

(75) Inventors: Gary S. Jacob, St. Louis, MO (US); Timothy M. Block, Doylestown, PA (US); Raymond A. Dwek, Oxford (GB)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 09/355,446

(22) PCT Filed: Feb. 12, 1998

(86) PCT No.: PCT/US98/03004

§ 371 (c)(1),
(2), (4) Date: Jan. 19, 2000

(87) PCT Pub. No.: WO98/35685

PCT Pub. Date: Aug. 20, 1998

(51) Int. Cl.[7] .................... A61K 31/00; A61K 31/675; A61K 31/51
(52) U.S. Cl. ................... 514/45; 514/42; 514/43; 514/45; 514/46; 514/47; 514/48; 514/49; 514/50; 514/51; 514/89; 514/277
(58) Field of Search ................... 514/42, 43, 45, 514/46, 47, 48, 49, 50, 51, 89, 277

(56) References Cited

U.S. PATENT DOCUMENTS

| | | | |
|---|---|---|---|
| 3,590,028 A | 6/1971 | Arcamone | 260/210 |
| 4,012,448 A | 3/1977 | Smith et al. | 260/591 |
| 4,065,562 A | 12/1977 | Ohata et al. | 424/267 |
| 4,182,767 A | 1/1980 | Murai et al. | 424/267 |
| 4,260,622 A | 4/1981 | Junge et al. | 424/267 |
| 4,269,857 A | 5/1981 | Tokuda et al. | 424/325 |
| 4,327,725 A | 5/1982 | Cortese et al. | 128/260 |
| 4,524,060 A | 6/1985 | Mughal et al. | 424/19 |
| 4,533,668 A | 8/1985 | Matsumura et al. | 514/321 |
| 4,611,058 A | 9/1986 | Koebernick | 546/242 |
| 4,612,008 A | 9/1986 | Wong et al. | 604/892 |
| 4,639,436 A | 1/1987 | Junge et al. | 514/24 |
| 4,765,989 A | 8/1988 | Wong et al. | 424/473 |
| 4,783,337 A | 11/1988 | Wong et al. | 424/468 |
| 4,806,650 A | 2/1989 | Schröder et al. | 546/242 |
| 4,849,430 A | 7/1989 | Fleet et al. | 514/315 |
| 4,880,830 A | 11/1989 | Rhodes | 424/470 |
| 4,940,705 A | 7/1990 | Böshagen et al. | |
| 4,957,926 A | 9/1990 | Jacob et al. | 514/315 |
| 5,003,072 A | 3/1991 | Partis et al. | 546/243 |
| 5,011,829 A | 4/1991 | Hirsch et al. | 514/50 |
| 5,030,638 A | 7/1991 | Partis et al. | 514/315 |
| 5,041,441 A | 8/1991 | Radin et al. | 514/237.8 |
| 5,051,407 A | 9/1991 | Böshagen et al. | |
| 5,068,112 A | 11/1991 | Samejima et al. | 424/495 |
| 5,144,037 A | 9/1992 | Partis et al. | 546/116 |
| 5,151,519 A | 9/1992 | Behling et al. | 546/219 |
| 5,190,765 A | 3/1993 | Jao et al. | 424/473 |
| 5,221,746 A | 6/1993 | Partis et al. | 546/220 |
| 5,264,356 A | 11/1993 | Rohrschneider | 435/236 |
| 5,281,724 A | 1/1994 | Behling et al. | 549/334 |
| 5,310,745 A | 5/1994 | Partis et al. | 514/315 |
| 5,331,096 A | 7/1994 | Koszyk et al. | 546/115 |
| 5,411,970 A | 5/1995 | Partis et al. | 514/315 |
| 5,451,679 A | 9/1995 | Barta et al. | 546/219 |
| 5,472,969 A | 12/1995 | Platt et al. | 514/315 |
| 5,491,135 A | 2/1996 | Blough | 514/115 |
| 5,525,616 A | 6/1996 | Platt et al. | 514/315 |
| 5,536,732 A | 7/1996 | Lesur et al. | 514/317 |
| 5,595,981 A | 1/1997 | Barta et al. | 514/63 |
| 5,612,480 A | 3/1997 | Barta et al. | 544/180 |
| 5,622,972 A | 4/1997 | Bryant et al. | 514/315 |
| 5,663,342 A | 9/1997 | Barta et al. | 546/6 |
| 5,703,058 A | * 12/1997 | Schinazi et al. | |
| 5,905,068 A | * 5/1999 | Chen et al. | 514/19 |
| 6,093,702 A | 7/2000 | Malley et al. | 514/45 |

FOREIGN PATENT DOCUMENTS

| | | | |
|---|---|---|---|
| DE | 4307883 A1 | 9/1993 | |
| EP | 0 324 328 | 7/1989 | ......... A61K/31/445 |
| EP | 0 350 012 | 1/1990 | ......... A61K/31/445 |
| EP | 0 367 748 | 5/1990 | ......... C07D/211/46 |
| EP | 0 401 194 | 6/1990 | ......... A61K/31/70 |
| EP | 0 477 160 | 9/1991 | ......... C12P/17/04 |
| EP | 0 449 026 | 10/1991 | ......... C07D/491/04 |
| EP | 0 494 850 | 7/1992 | ......... C07D/211/46 |
| EP | 0 566 556 | 10/1993 | ......... C07D/211/40 |
| EP | 0 691 327 | 3/1994 | ......... C07C/217/28 |
| EP | 0 729 747 | 2/1996 | ......... A61K/7/48 |
| FR | 2700267 | 1/1993 | ......... A61K/9/107 |
| GB | 2020278 | 3/1979 | ......... C07D/211/40 |
| WO | WO87/03903 | 7/1987 | ......... C12N/05/00 |
| WO | WO91/03242 A1 | 3/1991 | |
| WO | WO91/17145 | 11/1991 | ......... C07D/211/46 |
| WO | WO93/18763 | 9/1993 | ......... A61K/31/195 |
| WO | WO94/04546 | 3/1994 | ......... C07H/17/02 |
| WO | WO95/06061 | 3/1995 | ......... C07K/5/03 |

(List continued on next page.)

OTHER PUBLICATIONS

Dalton, et al., "A Phase II Randomized Study of Oral Verapamil as a Chemosensitizer to Reverse Drug Resistance in Patients with Refractory Myeloma," Feb. 1, 1995, Cancer, vol. 75, No. 3, pp. 815–820.

(List continued on next page.)

Primary Examiner—James O. Wilson
(74) Attorney, Agent, or Firm—Senniger, Powers, Leavitt & Roedel; J. Timothy Keane; Scott J. Meyer

(57) ABSTRACT

Provided are methods and compositions for treating hepatitis virus infections in mammals, especially humans. The methods comprise (1) administering N-substituted-1,5-dideoxy-1,5-imino-D-glucitol compounds in combination with nucleoside antiviral agents, nucleotide antiviral agents, mixtures thereof, or immunomodulating/immunostimulating agents, or (2) administering N-substituted-1,5-dideoxy-1,5-imino-D-glucitol compounds in combination with nucleoside antivirals agents, nucleotide antiviral agents, or mixtures thereof, and immunomodulating/immunostimulating agents.

55 Claims, 3 Drawing Sheets

FOREIGN PATENT DOCUMENTS

| WO | WO95/19172 | 7/1995 | ......... A61K/31/445 |
|---|---|---|---|
| WO | WO95/22975 | 8/1995 | ......... A61K/31/445 |
| WO | WO96/40110 | 12/1996 | .......... A61K/31/35 |
| WO | WO97/00881 | 1/1997 | ........... C07H/17/02 |
| WO | WO98/35685 | 8/1998 | .......... A61K/31/70 |
| WO | WO99/29321 | 6/1999 | ......... A61K/31/445 |
| WO | WO99/40916 | 8/1999 | ......... A61K/31/445 |
| WO | WO00/47198 A2 | 8/2000 | |

OTHER PUBLICATIONS

Jacob et al., "Aminosugar Attenuation of HIV Infection," 1992, Natural Products as Antiviral Agents, pp. 137–152.

Karpas, et al., "Aminosugar Derivatives as Potential Anti–Human Immunodeficiency Virus Agents," Dec., 1988, Proc. Natl. Acad. Sci., vol. 85, pp. 9229–9233.

Welsh, et al., "Accumulation of Fatty Alcohol in MCF–7 Breast Cancer Cells," Nov. 15, 1994, Archives of Biochemistry and Biophysics, vol. 315, No. 1, pp. 41–47.

Blum et al., "Antiviral Therapy of Hepatitis B Virus Infection: Blocking Viral Gene Expression," Jun. 1995, Elsevier Science, B.V., Advanced Drug Delivery Reviews 17, pp. 321–331.

Lu, et al., "Aberrant Trafficking of Hepatitis B Virus Glycoproteins in Cells in Which N–glycan Processing is Inhibited," Mar. 1997, Proc. Natl. Acad. Sci., vol. 94, pp. 2380–2385.

Korba, et al., "Antiviral Effectiveness of 3TC, Famciclovir, and Interferon Against Chronic WHV Replication–Potential for Combination Therapy," Sep. 1996, Molecular Biology of Hepatitis B Viruses Meeting, p. 201.

Lavie, et al., "Agents that Reverse Multidrug Resistance, Tamoxifen, Verapamil, and Cyclosporin A, Block Glycosphingolipid Metabolism by Inhibiting Ceramide Glycosylation in Human Cancer Cells," Aug. 20, 1996, The Journal of Biological Chemistry, vol. 272, No. 3, pp. 1682–1687.

Lavie et al., "Acculumation of Glucosylceramides in Multidrug–Resistant Cancer Cells," Aug. 9, 1996, The Journal of Biological Chemistry, Vo. 271, No. 32, pp. 19530–19536.

Inokuchi, et al., "Antitumor Activity Via Inhibition of Glycosphingolipid Biosynthesis," Sep. 3, 1987, Cancer Letters, vol. 38, pp. 23–30.

Dienstag, et al., "A Preliminary Trial of Lamivudine for Chronic Hepatitis B Infection," Dec. 21, 1995, The New England Journal of Medicine, vol. 333, No. 25, pp. 1657–1661.

Holleran, et al., "Characterization of Cellular Lipids in Doxorubicin–Sensitive and –Resistant P388 Mouse Leukemia Cells," 1986, Cancer Chemother Pharmacol, 17:11–15.

Fisher, et al., "Clinical Studies with Modulators of Multidrug Resistance," Apr. 1995, Drug Resistance in Clinical Oncology and Hematology, vol. 9, No. 2, pp. 363–382.

Raderer, et al., "Clinical Trials of Agents that Reverse Multidrug Resistance," Dec. 15, 1993, Cancer, vol. 72, No. 12, pp. 3553–3563.

Tan, et al., "Chemical Modification of the Glucosidase Inhibitor 1–Deoxynojirimycin," Aug. 5, 1991, The Journal of Biological Chemistry, Vo. 266, No. 22, pp. 14504–14510.

Wang, et al., "Chemo–enzymatic Synthesis of Five–membered Azasugars as Inhibitors of Fucosidase and Fucosyltransferase: An Issue Regarding The Stereochemistry Discrimination at Transition States," 1993, Tetrahedron Letters, vol. 34, No. 3, pp. 403–406.

Jezowska–Bojczuk, et al., "Copper(II) Interactions with an Experimental Antiviral Agent, 1–Deoxynojirimycin, and Oxygen Activation by Resulting Complexes," 1996, Journal of Inorganic Biochemistry, vol. 64, pp. 231–246.

Ramu, et al., "Differences in Lipid Composition of Doxorubicin–Sensitive and –Resistant P388 Cells," Apr. 1984, Cancer Treatment Reports, vol. 68, No. 4, pp. 637–641.

Beketic–Oreskovic, et al., "Decreased Mutation Rate for Cellular Resistance to Doxorubicin and Suppression of mdr1 Gene Activation by the Cyclosporin PSC 833," Nov. 1, 1995, Journal of the National Cancer Institute, vol. 87, No. 21, pp. 1593–1602.

Coates, et al., "Developments in Viral Hepatitis During 1994," 1995, Exp. Opin. Ther. Patents, 5(8): 747–756.

Korba, et al., "Effectiveness of Combination Therapies with 3TC, Famciclovir, and Alpha Interferon Against Woodchuck Hepatitis Virus Replication in Chronically–infected Woodchucks: Model for Potential Anti–HBV Treatments," Apr. 1997, Antiviral Research, vol. 34, No. 2, p. A52.

Volm, et al., "Expression of Resistance Factors (P–Glycoprotein, Glutathione S–Transferase-$_{\pi}$, and Topoisomerase II) and Their Interrelationship to Proto–Oncogene Products in Renal Cell Carcinomas," Jun. 15, 1993, Cancer, vol. 71, No. 12, pp. 3981–3987.

Lu, et al., "Evidence That N–Linked Glycosylation is Necessary for Hepatitis B Virus Secretion," Nov. 10, 1995, Virology, vol. 213, No. 2, pp. 660–665.

Wiltink, "Future Prospects in Antiviral Therapy," Jun. 1992, Pharmaceutisch Weekblad Scientific Edition, 14(4A), pp. 268–274.

Bolhuis, et al., "Mechanisms of Multidrug Transporters," 1997, FEMS Microbiology Reviews 21, pp. 55–84.

Legler, et al., "Glycosylceramidase from Calf Spleen: Characterization of its Active Site with 4–n–Alkylurnbelliferyl β–glucoside and N–alkyl Derivatives of 1–Deoxynojirimycin," Dec. 1985, Bio–ChemHoppe–Seyler, vol. 366, pp. 1113–1122.

Hardman, et al., "Goodman & Gilman's The Pharmacological Basis of Therapeutics," 1996, McGraw–Hell, Ninth Edition, Chapter 32: Drugs Used for the Treatment of Myocardial Ischemia, Verepemil, pp. 767–774, 780–781, 799–801, and 829.

Mehta, et al., Hepatitis B Virus (HBV) Envelope Glycoproteins Vary Drastically in Their Sensitivity to Glycan Processing: Evidence that Alteration of a Single N–Linked Glycosylation Site Can Regulate HBV Secretion, Mar. 1997, Proc. Natl. Acad. Sci., vol. 94, pp. 1822–1827.

Locarnini, et al., "Hepatitis B: New Approaches for Antiviral Chemotherapy," 1996 Antiviral Chemistry & Chemotherapy, 7(2), pp. 53–64.

Doong, et al., "Inhibition of the Replication of Hepatitis B Virus In Vitro by 2',3'–dideoxy–3'–thiacytidine and Related Analogues," Oct. 1991, Proc. Natl. Acad. Sci., vol. 88, pp. 8495–8499.

Fleet, et al., "Inhibition of HIV Replication by Amino–Sugar Derivatives," Sep. 1988, Federation of European Biochemical Societies, vol. 237, No. 1,2, pp. 128–132.

Newbrun, et al., "Inhibition by Acarbose, Nojirimycin and 1–Deoxynojirimycin of Glucosyltransferase Produced by Oral Streptococci," 1983, Archs Oral Biol., vol. 28, No. 6, pp. 531–536.

Saunier, et al., "Inhibition of N–Linked Complex Oligosaccharide Formation by 1–Deoxynojirimycin, An Inhibitor of Processing Glucosidases," Dec. 10, 1982, The Journal of Biological Chemistry, vol. 257, No. 23, pp. 14155–14161.

Abe, et al., "Induction of Glycosylceramide Synthase by Synthase Inhibitors and Ceramide," 1996, Biochemica et Biophysica Acta, vol. 1299, pp. 333–341.

Abe, et al., "Improved Inhibitors of Glucosylceramide Synthase," 1992, J. Biochem., vol. 111, pp. 191–196.

Tan, et al., "Introduction of Oxygen into the Alkyl Chain of N–decyl–dNM Decreases Lipophilicity and Results in Increased Retention of Glucose Residues on N–Linked Oligosaccharides," 1994, Glycobiology, vol. 4, No. 2, pp. 141–149.

Elbein, "Inhibitors of the Biosynthesis and Processing of N–Linked Oligosaccharide Chains," 1987, Ann. Rev. Biochem., 56:497–534.

Radin, et al., "Inhibitors of Cerebroside Metabolism," 1981, Methods in Enzymology, vol. 72, pp. 673–684.

Prence, et al., "In Vitro Accumulation of Glucocerebroside in Neuroblastoma Cells: A Model for Study of Gaucher Disease Pathobiology," 1996, Journal of Neuroscience Research, 43:365–371.

Korba, "In Vitro Evaluation of Combination Therapies Against Hepatitis B Virus Replication," 1995, Antiviral Research, vol. 29, pp. 49–51.

Bradley, et al., "Mechanism of Multidrug Resistance," 1988, Biochimica et Biophysica Acta, vol. 948, pp. 87–128.

Mülder, et al., "Multidrug Resistance–Modifying Components in Human Plasma with Potential Clinical Significance," Jan. 1996, Journal of Experimental Therapeutics & Oncology, vol. 1, No. 1, pp. 13–22.

Ardalan, et al., "Mechanism of Action of a New Antitumor Agent, Carbetimer," Nov. 1986, Cancer Research, vol. 46, pp. 5473–5476.

Platt, et al., "Modulation of Cell–Surface Transferrin Receptor by the Imino Sugar N–butyldeoxynojirimycin," 1992, Eur. J. Biochem., vol. 208, pp 187–193.

Kawakami, et al., "Monoclonal Antibodies with Affinity to Self–Complementary Left–Handed DNA Containing Cyclonucleosides with High Anti Conformation," 1994, Nucleosides & Nucleotides, vol. 13(1–3), pp. 421–427.

Dicato, et al., "Multidrug Resistance: Molecular and Clinical Aspects," 1997, Cytokines, Cellular & Molecular Therapy, vol. 3, No. 2, pp. 91–100.

Bolhuis, et al., "Mechanisms of Multidrug Transporters," 1997, FEMS Microbiology Reviews, vol. 21, pp. 55–84.

Platt, et al., "N–Butyldeoxynojirimycin Is a Novel Inhibitor of Glycolipid Biosynthesis: Secretion of Human Hepatitis B Virus Is Inhibited by the Imino Sugar N–Butyldeoxynojirimycin," 1994, Chemtracts–Organic Chemistry, vol. 7, pp. 106–107.

Platt, et al., "N–Butyldeoxynojirimycin Is a Novel Inhibitor of Glycolipid Biosynthesis," Mar. 18, 1994, The Journal of Biological Chemistry, vol. 269, No. 11, pp. 8362–8365.

Platt, et al., "N–Butyldeoxygalactonojirimycin Inhibits Glycolipid Biosynthesis but Does Not Affect N–Linked Oligosaccharide Processing," Oct. 28, 1994, The Journal of Biological Chemistry, vol. 269, No. 43, pp. 27108–27114.

Platt, et al., "New Approach for the Treatment of Gauchers Disease," Mar. 1996, Gauchers Association Newsletter, one page.

Wilson, et al., "Nitrogen Glycosylation Reactions Involving Pyrimidine and Purine Nucleoside Bases with Furanoside Sugars," Dec. 1995, Synthesis, Department of Chemistry, Emory University, pp. 1465–1479.

Kers, et al., "Nucleoside Phosphonates. Development of Synthetic Methods and Reagents," 1996, Nucleosides & Nucleotides, 15(1–3), pp. 361–378.

Tsuruo, et al., "Overcoming of Vincristine Resistance in P388 Leukemis In Vivo and In Vitro Enhanced Cytotoxicity of Vincristine and Vinblastine by Verapamil," May 1981, Cancer Research, vol. 41, pp. 1967–1972.

Wright, et al., "Phospholipid and Ether Linked Phospholipid Content Alter with Cellular Resistance to Vinblastine," Dec. 17, 1985, Biochemical and Biophysical Research Communications, vol. 133, No. 2, pp. 539–545.

Bradley, et al., "P–glycoprotein, Multidrug Resistance and Tumor Progression," 1994, Cancer and Metastasis Reviews, vol. 13, pp. 223–233.

May, et al., "Plasma Membrane Lipid Composition of Vinblastine Sensitive and Resistant Human Leukaemic Lymphoblasts," 1988, Int. J. Cancer, vol. 42, pp. 728–733.

Mutchnick, et al., "Prospectives on the Treatment of Chronic Hepatitis B and Chronic Hepatitis C with Thymic Peptides and Antiviral Agents," 1994, Antiviral Research, vol. 24, pp. 245–257.

Platt, et al., "Prevention of Lysosomal Storage in Tay–Sachs Mice Treated with N–Butyldeoxynojirimycin," Apr. 18, 1997, Science, vol. 276, pp. 428–431.

Wishart, et al., "Quinidine as a Resistance Modulator of Epirubicin in Advanced Breast Cancer: Mature Results of a Placebo–Controlled Randomized Trial," Sep. 1994, Journal of Clinical Oncology, vol. 12, No. 9, pp. 1771–1777.

Chabner, et al., "Reversal of Multidrug Resistance," Jan. 1991, Journal of Clinical Oncology, vol. 9, No. 1, pp. 4–6.

Hui, et al., "Reduced p21$^{WAF1/CIP1}$ Expression and p53 Mutation in Hepatocellular Carcinomas," Mar. 1997, Hepatology, vol. 25, No. 3, pp. 575–579.

Radin, "Rationales for Cancer Chemotherapy with PDMP, a Specific Inhibitor of Glucosylceramide Synthase," 1994, Molecular and Chemical Neuropathology, vol. 21, pp. 111–127.

Arends, "Recueil des Travaux Chimiques des Pays–Bas," Journal of the Royal Netherlands Chemical Society, Feb. 1994, Recl. Trav. Chim. Pays–Bas 113, 63–114, contents page only.

Shukla, et al., "Rapid Kidney Changes Resulting from Glycosphingolipid Depletion by Treatment with a Glucosyltransferase Inhibitor," 1991, Biochemica et Biophysica Acta., vol. 1083, pp. 101–108.

Rosina, et al., "Recent Developments in the Treatment of Hepatitis D Infection," 1996, Anti–infectives—Section Review, Exp. Opin. Invest. Drugs, No. 5(2), pp. 197–205.

Gish, et al., "Recent Developments in the Treatment of Chronic Hepatitis B Virus Infection," 1995, Exp. Opin. Invest. Drugs, 4(2), pp. 95–115.

Block, et al., "Secretion of Human Hepatitis B Virus is Inhibited by the Imino Sugar N–butyldeoxynojirimycin," Mar. 1994, Proc. Natl. Acad. Sci., vol. 91, pp. 2235–2239.

Inokuchi, et al., "Stimulation of Glycosphingolipid Biosynthesis by L–Threo–1–Phenyl–2–Decanoylamino–1–Propanal and Its Homologs in B16 Melanoma Cells," 1995, J. Biochem., vol. 117, No. 4, pp. 766–773.

Abe, et al., "Structural and Stereochemical Studies of Potent Inhibitors of Glucosylceramide Synthase and Tumor Cell Growth," 1995, Journal of Lipid Research, vol. 36, pp. 611–621.

Ogawa, et al., "Synthesis of Potent β–D–Glucocerebrosidase Inhibitors: N–Alkyl–β–Valienamines," 1996, Bioorganic & Medicinal Chemistry Letters, vol. 6, No. 8, pp. 929–932.

Vorbrüggen, et al., "Some Recent Trends and Progress in Nucleoside Synthesis," 1996, Acta Biochimica Polonica, vol. 43, No. 1, pp. 25–36.

Sobrero, et al., "Sequential Dichloromethotrexate (DCM) and 5–Fluorouracil (FU): A Synergistic Combination Potentially Valuable for Hepatic Artery Infusion Therapy," Mar. 1983, ASCO Abstracts, Clinical Pharmacology, vol. 2, Article C–102, p. 26.

Wadkins, et al., "The Role of Drug–Lipid Interactions in the Biological Activity of Modulators of Multi–Drug Resistance," 1993, Biochimica et Biophysica Acta, vol. 1153, pp. 225–236.

Doige, et al., "The Effects of Lipids and Detergents on ATPase–Active P–Glycoprotein," 1993, Biochimica et Biophysica Acta, vol. 1146, pp. 65–72.

Ries, et al., "Treatment of Advanced and Refractory Breast Cancer with Doxorubicin, Vincristine and Continuous Infusion of Verapamil. A Phase I–II Clinical Trial," 1991, Med. Oncol. & Tumor Pharmacother, vol. 8, No. 1, pp. 39–43.

Dusheiko, "Treatment and Prevention of Chronic Viral Hepatitis," 1995, Pharmac. Ther., vol. 65, pp. 47–73.

Block, et al., "Treatment of Chronic Hepadnavirus Infection in a Woodchuck Animal Model with an Inhibitor of Protein Folding and Trafficking," May 1998, Nature Medicine, vol. 4, No. 5, pp. 610–614.

Repp, et al., "The Effects of Processing Inhibitors of N–Linked Oligosaccharides on the Intracellular Migration of Glycoprotein E2 of Mouse Hepatitis Virus and the Maturation of Coronavirus Particles," Dec. 15, 1986, The Journal of Biological Chemistry, vol. 260, No. 29, pp. 15873–15879.

Radin, et al., "Treatment of Gaucher Disease with an Enzyme Inhibitor," 1996, Glycoconjugate Journal, vol. 13, pp. 153–157.

Fischl, et al., "The Safety and Efficacy of Combination N–Butyl–Deoxynorjirimycin (SC–48334) and Zidovudine in Patients with HIV–1 Infection and 20—500 CD4 Cells/$mm^3$," 1994, Journal of Acquired Immune Deficiency Syndromes, vol. 7, pp. 139–147.

Mutchnick, et al., "Thymosin Treatment of Chronic Hepatitis B: A Placebo–controlled Pilot Trial," 1991, Hepatology, vol. 14, No. 3, pp. 409–415.

Simon, et al., "Treatment of Chronic Hepatitis C with Interferon Alfa–n3: A Multicenter, Randomized, Open–Label Trial," Feb. 1997, Hepatology, vol. 25, No. 2, pp. 445–448.

Rhodes, "Therapeutic Potential of Schiff Base–forming Drugs," 1996, Exp. Opin. Invest. Drugs, 5(3), pp. 257–268.

Cabot, et al., "Tamoxifen Retards Glycosphingolipid Metabolism in Human Cancer Cells," 1996, FEBS Letters (17548), vol. 394, pp. 129–131.

Lindsay, et al., "Thymosin $\alpha_1$ Treatment of Chronic Hepatitis B: A Multicenter, Randomized, Placebo–Controlled Double Blind Study," Apr. 1995, AASLD, A1127, one page.

Mutchnick, et al., "Thymosin Treatment of Chronic Active Hepatitis B (CAHB): A Preliminary Report on a Controlled, Double Blind Study," 1988, Hepatology, vol. 8, No. 5, Article 208, p. 1270.

van den Broek, et al., "Synthesis of Oxygen–Substituted N–alkyl 1–deoxynojirimycin derivatives: aza sugar α–glucosidase inhibitors showing antiviral (HIV–1) and immunosuppressive activity," Recl. Trav. Chim. Pays–Bas 113, 1994, pp. 507–516.

Dwek, Raymond, "Glycobiology: Toward Understanding the Function of Sugars," Chem. Rev. 1996, 96, pp. 683–720.

Platt, Frances M., et al., "Inhibitors of Glycosphingolipid Biosynthesis," Trends in Glycoscience and Glycotechnology, vol. 7, No. 38, Nov. 1995, pp. 495–511.

Mutchnick, et al., "Thymosin Treatment of Chronic Active Hepatitis B (CAHB): Results of a Pilot Study," Hepatology, vol. 10, No. 4, 1989.

Acosta et al., "Agents for Treating Human Immunodeficiency Virus Infection," AM. J. Hosp. Pharm., vol. 51, Sep. 15, 1994, pp. 2251–2287.

Tennant, et al., "Animal Models in the Preclinical Assessment of Therapy for Viral Hepatitis," Antiviral Therapy, vol. 1, (Suppl.4), 1996, pp. 47–52.

Sachs, "Antiretroviral Chemotherapy of Human Immunodeficiency Virus Infections Other Than with Azidothymidine," Arch. Inter. Med., vol. 152, Mar. 1992, pp. 485–504.

Gasparini, et al., "Clinical Importance of the Determination of Tumor Angiogenesis of Breast Carcinoma: Much More Than a New Prognostic Tool," Journal of Clinical Oncology, vol. 13, No. 3, Mar. 1995, pp. 765–782.

Bruyneel, et al., "Effect of Glycosylation Inhibitors on N–Glycosylpeptides and on invasion of Malignant Mouse $MO_4$ Cells in Virto," Journal of Cell Science, vol. 95, 1990, pp. 279–286.

Jacob, "Glycosylation Inhibitors in Biology and Medicine," Current Opinion in Structural Biology, No. 5, 1995, pp. 605–611.

Senuma, et al., "Highly Efective Resolution of 1,3–Dibensl–6–hydroxy–3,3a,6,6a–tetrahydro–1H–furo[3,4–d]imidazole–2–4–dione, an Intermediate for Biotin, with Optically Active Amines and Reutilization of the Unwanted Epimer," Chem. Pharm. Bull., vol. 38, No. 4, 1990, pp. 882–887

Zitzmann, et al., "Imino Sugars Inhibit the Formation and Secretion of Bovine Viral Diarrhea Virus, a Pestivirus Model of Hepatits C Virus: Implications for the Development of Broad Spectrum Anti–Hepatitis Virus Agents," PNAS, vol. 96, No. 21, Oct. 12, 1999, pp. 11878–11882.

Rusconi, et al., "Inhibition of Human Immunodficiency Virus Type I Replication in Cytokine–Stimulated Monocytes/Macrophages by Combination Therapy," Journal of Infectious Diseases, vol. 170, 1994, pp. 1361–1366.

Goss, et al., "Inhibition of Carbohydrate Processing: A New Class of Anticancer Agents," Clinical Cancer Research, vol. 1, Sep. 1995, pp. 935–944.

Isom, et al., "Molecular Pathology of Human Oncogenic Ciruses," Cellular and Molecular Pathogenesis, Chapter 14, 1996, pp. 341–387.

Ratner, et al., "Mechanism of Action of N–Butyl Deoxynojirimycin in Inhibiting HIV–1 Infection and Activity in Combination with Nucleoside Analogs," AIDS Research and Human Retroviruses, vol. 9, No. 4, 1993, pp. 291–297.

Myers, "New Antiretroviral Agents in the Clinic," Reviews of Infectious Diseases, vol. 12, No. 5, Sep./Oct. 1990, pp. 944–950.

Mitts, et al., "The Reaction of Glucose with Some Amines," Journal of the American Chemical Society, vol. 66, Mar. 1944, pp. 483–486.

Lino, "Treatment of Chronic Viral Hepatitis," Mol. Med. (Tokyo), 1996, Vol. 33, No. 3, pp. 276–286 (English language abstract only).

Fiume, et al., "Targeting of Antiviral Drugs to the Liver Using Glycoprotein Carriers," Advanced Drug Delivery Reviews, vol. 14, 1994, pp. 51–65.

Jones, et al., "Use of the Topliss Scheme for the Design of More Effective Chelating Agents for Cadmium Decorporation," Chem. Res. Toxicol., vol. 1, 1988, pp. 234–237.

Karrer, et al., "Zur Kenntis der Reduktionsprodukte aus Aromatischen Aminen und Zuckern," 1935, pp. 1338–1340.

Block et al., Proc. Natl. Acad. Sci. USA, (Mar. 1994), vol. 91, pp. 2236–2239.*

Mueller, R. et al., "Use of N–substituted–1,5–dideoxy–1, 5–imino–D–glucitol compounds for treating hepatitis virus infections," CA 135:175348, 2001.

* cited by examiner-

METHODS OF TREATING HEPATITIS VIRUS INFECTIONS WITH N-SUBSTITUTED-1,5-DIDEOXY-1,5-IMINO-D-GLUCITOL COMPOUNDS IN COMBINATION THERAPY

BACKGROUND OF THE INVENTION

1. Field of the Invention

The present invention relates to methods and compositions for treating hepatitis virus infections, especially hepatitis B virus infections, in mammals, especially humans. The methods comprise (1) administering N-substituted-1,5-dideoxy-1,5-imino-D-glucitol compounds in combination with nucleoside antiviral agents, nucleotide antiviral agents, mixtures thereof, or immunomodulating/-immunostimulating agents, or (2) administering N-substituted-1,5-dideoxy-1,5-imino-D-glucitol compounds in combination with nucleoside antiviral agents, nucleotide antiviral agents, or mixtures thereof, and immunomodulating/immunostimulating agents. Such combinations of anti-hepatitis viral agents show unexpected efficacy in inhibiting replication and secretion of hepatitis viruses in cells of mammals infected with these viruses.

2. Description of Related Art

Hepatitis Viruses

Hepatitis B Virus (HBV, HepB) is a causative agent of acute and chronic liver disease including liver fibrosis, cirrhosis, inflammatory liver disease, and hepatic cancer that can lead to death in some patients (Joklik, Wolfgang K., *Virology*, Third Edition, Appleton & Lange, Norwalk, Conn., 1988 (ISBN 0-8385-9462-X)). Although effective vaccines are available, there are still more than 300 million people worldwide, i.e., 5% of the world's population, chronically infected with the virus (Locarnini, S. A., et. al., *Antiviral Chemistry & Chemotherapy* (1996) 7(2):53–64). Such vaccines have no therapeutic value for those already infected with the virus. In Europe and North America, between 0.1% to 1% of the population is infected. Estimates are that 15% to 20% of individuals who acquire the infection develop cirrhosis or another chronic disability from HBV infection. Once liver cirrhosis is established, morbidity and mortality are substantial, with about a 5-year patient survival period (Blume, H., E., et.al., *Advanced Drug Delivery Reviews* (1995) 17:321–331). It is therefore necessary and of high priority to find improved and effective anti-HBV anti-hepatitis therapies (Locarnini, S. A., et. al., *Antiviral Chemistry & Chemotherapy* (1996) 7(2): 53–64).

Other hepatitis viruses significant as agents of human disease include Hepatitis A, Hepatitis B, Hepatitis C, Hepatitis Delta, Hepatitis E, Hepatitis F, and Hepatitis G (Coates, J. A. V., et.al., *Exp. Opin. Ther. Patents* (1995) 5(8): 747–756). In addition, there are animal hepatitis viruses that are species-specific. These include, for example, those infecting ducks, woodchucks, and mice.

1,5-dideoxy-1,5-imino-D-glucitol Compounds 1,5-dideoxy-1,5-imino-D-glucitol (also known as 1-deoxynojirimycin, DNJ) and its N-alkyl derivatives are known inhibitors of the N-linked oligosaccharide processing enzymes alpha glucosidase I and II (Saunier et al., *J. Biol. Chem.* (1982) 257:14155–14161 (1982); Elbein, *Ann. Rev. Biochem.* (1987) 56:497–534). As glucose analogs, they also have potential to inhibit glucose transport, glucosyl-transferases, and/or glycolipid synthesis (Newbrun et al., *Arch. Oral Biol.* (1983) 28: 516–536; Wang et al., *Tetrahedron Lett.* (1993) 34:403–406). Their inhibitory activity against glucosidases has led to the development of these compounds as anti-hyperglycemic agents and antiviral agents. See, for example, PCT International Publication WO 87/03903 and U.S. Pat. Nos. 4,065,562; 4,182,767; 4,533, 668; 4,639,436; 4,849,430; 4,957,926; 5,011,829; and 5,030, 638.

Glucosidase inhibitors such as N-alkyl-1,5-dideoxy-1,5-imino-D-glucitol compounds wherein the alkyl group contains between three and six carbon atoms have been shown to be effective in the treatment of Hepatitis B infection (PCT International Publication WO 95/19172). For example, n-butyl-deoxynojirimycin (n-butyl-DNJ; N-butyl-1–5-dideoxy-1,5-imino-D-glucitol) is effective for this purpose (Block, T. M., *Proc. Natl. Acad. Sci. USA* (1994) 91:2235–2239; Ganem, B. Chemtracts: *Organic Chemistry* (1994) 7(2), 106–107). N-butyl-DNJ has also been tested as an anti-HIV-1 agent in HIV infected patients, and is known to be well tolerated. Another alpha glucosidase inhibitor, deoxynojirimycin (DNJ), has been suggested as an antiviral agent for use in combination with N-(phosphonoacetyl)-L-aspartic acid (PALA) (WO 93/18763). However, combinations of N-substituted-imino-D-glucitol derivatives and other antiviral agents for the treatment of hepatitis virus infections have not been previously disclosed or suggested.

Nucleoside and Nucleotide Antiviral Agents

Reverse transcriptase inhibitors, including the class of nucleoside and nucleotide analogs, were first developed as drugs for the treatment of retroviruses such as human immunodeficiency virus (HIV), the causative agent of AIDS. Increasingly, these compounds have found use against other viruses, including both RNA and DNA viruses, via viral screening and chemical modification strategies. Nucleoside and nucleotide analogs exert their antiviral activities by inhibiting the corresponding DNA and RNA polymerases responsible for synthesis of viral DNA and RNA, respectively. Because viruses contain different forms of polymerases, the same nucleoside/nucleotide compound can have a dramatically different effect against different viruses. For example, lamivudine (3TC™) appears to be useful against HBV infection, whereas zidovudine (AZT™) appears to have little use against the same virus (Gish, R. G., et al., *Exp. Opin. Invest. Drugs* (1995) 4(2) :95–115)

Toxicity has been significant with some nucleoside analog antivirals. For example, clinical tests on the use of the nucleoside analog fialuridine (FIAU) for treatment of chronic hepatitis B were suspended recently due to drug-related liver failure leading to death in some patients. Consequently, there is still a need for safer drug regimens for the treatment of hepatitis B infections and hepatitis (Mutchnick, M. G., et. al., *Antiviral Research* (1994) 24:245–257).

Immunomodulators and Immunostimulants

Immunomodulators/immunostimulators such as interferon alfa and other cytokines have been used for the treatment of HBV infection with promising results. Unfortunately, the response rates are lower than desired. Interferon treatment is currently approved by the FDA for the treatment of Hepatitis B. Other immune system-affecting drug candidates are presently being investigated. These include thymic pepides for use in the treatment of chronic hepatitis B (CHB), isoprinosine, steroids, Shiff base-forming salicylaldehyde derivatives such as Tucaresol, levamisol, and the like (Gish, R. G., et.al., *Exp. Opin. Invest. Drugs* (1995) 4(2):95–115; Coates, J. A. V., et.al., *Exp. Opin. Ther. Patents* (1995) 5(8) :747–765).

The use of N-substituted-imino-D-glucitol compounds in combination with immunomodulating/immunostimulating agents is novel.

SUMMARY OF THE INVENTION

As noted above, the combination of N-substituted-imino-D-glucitol compounds and derivatives thereof with other anti-hepatitis virus compounds has, to the present inventor's knowledge, neither been suggested nor disclosed. The use of two or more anti-viral agents to provide improved therapy for the treatment of hepatitis B virus infections is desirable due to the morbidity and mortality of the disease. Combination therapy is also desirable since it should reduce toxicity in patients as it enables the physician to administer lower doses of one or more of the drugs being given to a patient. Combination therapy can also help to prevent the development of drug resistance in patients (Wiltink, E. H. H., *Pharmaceutish Weekblads Scientific Edition* (1992) 14(4A):268–274). The result of an improved efficacy configuration combined with a relative lack of toxicity and development of resistance would provide a much improved drug treatment profile.

The present inventor has surprisingly discovered that the combined use of N-substituted-l,5-dideoxy-1,5-imino-D-glucitol compounds and nucleoside or nucleotide antiviral compounds, or combinations thereof, and/or immunomodulators/immunostimulants, results in unexpectedly greater anti-hepatitis virus effectiveness of the compounds compared to the combined antiviral activities expected of the individual compounds alone. Whether this is due to different mechanisms of action of the different classes of drugs employed or some other biological phenomenon is presently unclear.

Accordingly, in a first aspect, the present invention provides a method of treating a hepatitis virus infection in a mammal, comprising administering to said mammal a first amount of an N-substituted1,5-dideoxy-1,5-imino-D-glucitol compound of Formula I:

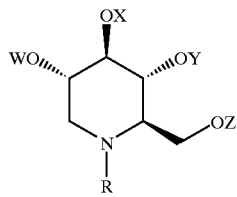

I wherein:

R is selected from the group consisting of arylalkyl, cycloalkylalkyl, and branched or straight chain alkyl having a chain length of $C_1$ to $C_{20}$, and W, X, Y, and Z are each independently selected from the group consisting of hydrogen, alkanoyl, aroyl, and trifluoroalkanoyl; and a second amount of an antiviral compound selected from the group consisting of a nucleoside antiviral compound, a nucleotide antiviral compound, and mixtures thereof, wherein said first and second amounts of said compounds together comprise an anti-hepatitis virus effective amount of said compounds.

In a second aspect, the present invention provides a method of treating a hepatitis-B virus infection in a mammal, comprising administering to said mammal from about 0.1 mg/kg/day to about 100 mg/kg/day of an N-substituted-1,5-dideoxy-1,5-imino-D-glucitol compound of Formula I, as above, and from about 0.1 mg/person/day to about 500 mg/person/day of a compound selected from the group consisting of a nucleoside antiviral compound, a nucleotide antiviral, and mixtures thereof.

The present invention also provides a method of treating a hepatitis B virus infection in a human patient, comprising administering to said human patient from about 0.1 mg/kg/day to about 100 mg/kg/day of N-(n-nonyl-)-1,5-dideoxy-1,5-imino-D-glucitol and from about 0.1 mg/person/day to about 500 mg/person/day of (−)-2'-deoxy-3'-thiocytidine-5'-triphosphate.

Also provided is a composition, comprising an N-substituted-1,5-dideoxy-1,5-imino-D-glucitol compound of Formula I, as above, and an antiviral compound selected from the group consisting of a nucleoside antiviral compound, a nucleotide antiviral compound, and mixtures thereof.

The invention also provides a pharmaceutical composition, comprising a first amount of an N-substituted-1,5-dideoxy-1,5-imino-D-glucitol compound of Formula I, as above, and a second amount of an antiviral compound selected from the group consisting of a nucleoside antiviral compound, a nucleotide antiviral compound, and mixtures thereof, as well as a pharmaceutically acceptable carrier, diluent, or excipient.

The invention further provides a pharmaceutical composition for treating a hepatitis B virus infection in a mammal, comprising from about 0.1 mg to about 100 mg of an N-substituted-1,5-dideoxy1,5-imino-D-glucitol compound of Formula I, as above, and from about 0.1 mg to about 500 mg of a compound selected from the group consisting of a nucleoside antiviral compound, a nucleotide antiviral, and mixtures thereof.

Also provided is a pharmaceutical composition for treating a hepatitis B virus infection in a human patient, comprising from about 0.1 mg to about 100 mg of N-(n-nonyl-)-1,5-dideoxy-1,5-imino-D-glucitol, and from about 0.1 mg to about 500 mg of (−)-2'-deoxy-3'-thiocytidine-5'-triphosphate.

In addition to the foregoing, the present invention also provides methods and compositions like those listed above, wherein the N-substituted-1,5-dideoxy-1,5-imino-D-glucitol compounds of Formula I, nucleoside antiviral compounds, nucleotide antiviral compounds, or mixtures of nucleoside and nucleotide antiviral compounds, are used in combination with immunomodulators, immunostimulators, or mixtures of immunomodulators and immunostimulators.

In another aspect, the present invention also provides methods and compositions like those listed before the paragraph immediately above, wherein the N-substituted-1,5-dideoxy1,5-imino-D-glucitol compounds of Formula I are used in combination with immunomodulators, immunostimulators, or mixtures of immunomodulators and immunostimulators, but without nucleoside antiviral compounds, nucleotide antiviral compounds, or mixtures of nucleoside and nucleotide antiviral compounds.

Further scope of the applicability of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only, and are not limitative of the present invention, in which.

DETAILED DESCRIPTION OF THE INVENTION

Figure 1:
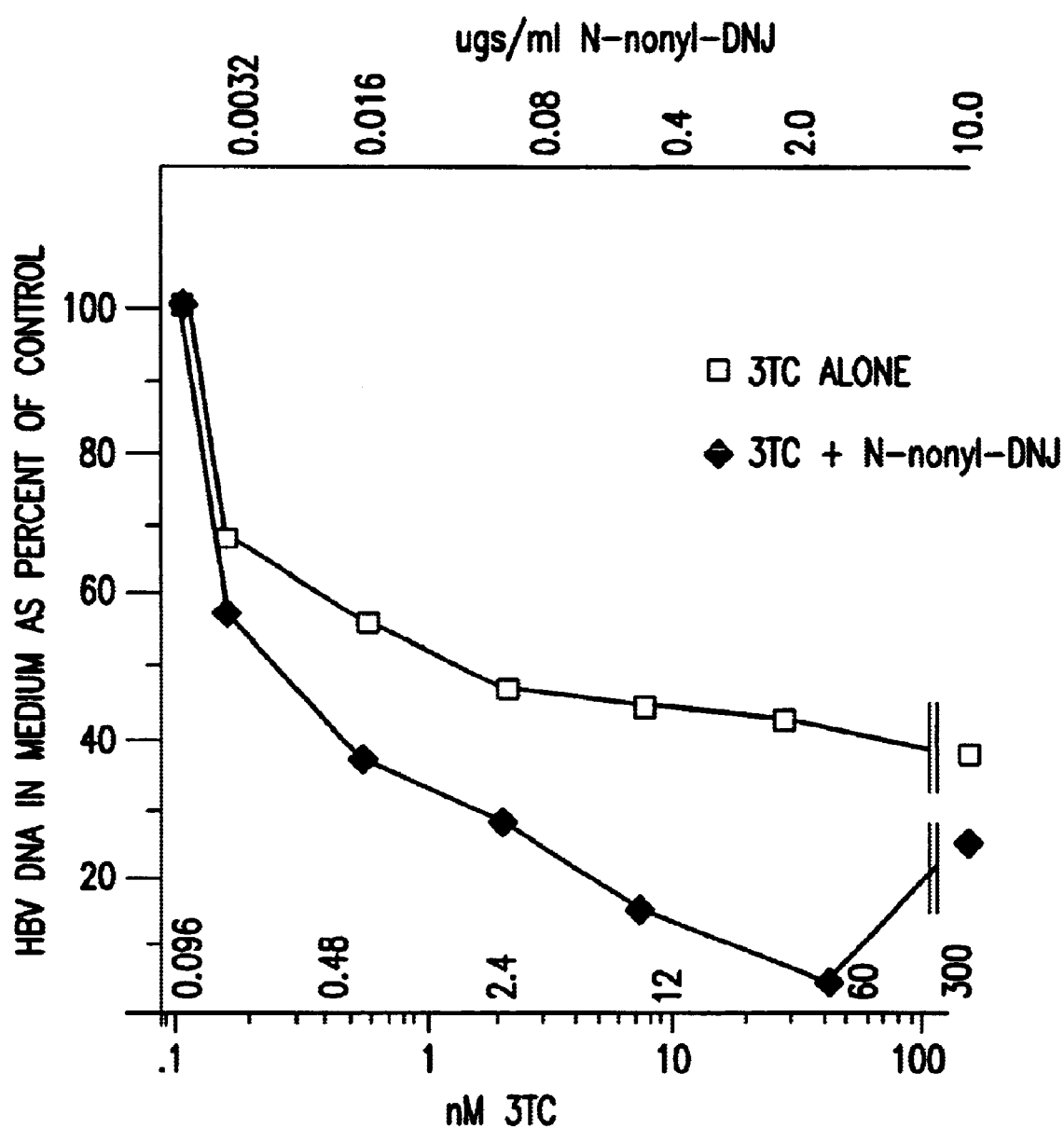
FIG. 1 shows the anti-hepatitis B virus activity of (−)-2'-deoxy-3'-thiocytidine-5'-triphosphate (3TC) alone and in combination with N-nonyl-DNJ in vitro.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

The present inventor has discovered that combinations of N-substituted1,5-dideoxy-i,5-imino-D-glucitol compounds with anti-hepatitis virus nucleoside or nucleotide analogs, and/or immunomodulators/-immunostimulants, are more effective in inhibiting hepatitis virus replication than that which would be expected via the combined use of the individual compounds.

The present invention thus provides pharmaceutical compositions and methods of treating hepatitis virus infections, especially hepatitis B virus infections, in humans, other mammals, and cells using a combination of an N-substituted-1,5-dideoxy-1,5-imino-D-glucitol compound with either an antiviral nucleoside, an antiviral nucleotide, mixtures thereof, and/or an immunomodulating or immunostimulating agent. The N-substituted-1,5-dideoxy-1,5-imino-D-glucitol compounds have basic nitrogen atoms and may be used in the form of a pharmaceutically acceptable salt. Nucleosides and nucleotides useful in the present invention are substituted purine or pyrmidine heterocycles further substituted with $R^1$ at the 9 position in the case of purines or with $R^1$ at the 1 position in the case of pyrimidines. The immunomodulating and immunostimulating agents useful in the present invention include those that stimulate immune responses effective in controlling or eliminating viruses or other infectious agents. Non-limiting examples of such immunomodulating and immunostimulating agents include cytokines, peptide agonists, steroids, and classic drugs such as levamisol. The drug combinations of this invention may be provided to a cell or cells, or to a human or other mammalian patient, either in separate pharmaceutically acceptable formulations, formulations containing more than one therapeutic agent, or by an assortment of single agent and multiple agent formulations. However administered, these drug combinations form an anti-hepatitis virus effective amount of components.

As used herein, the term "anti-hepatitis-virus effective amount" refers to a combined amount of (1) an N-substituted-1,5-dideoxy-1,5-imino-D-glucitol compound with either an antiviral nucleoside, an antiviral nucleotide, a mixture of an antiviral nucleoside and an antiviral nucleotide, or an immunomodulating/-immunostimulating agent (or mixtures thereof), or (2) a combined amount of an N-substituted-1,5-dideoxy-1,5-imino-D-glucitol compound with an antiviral nucleoside, an antiviral nucleotide, or a mixture thereof, and an immunomodulating/-immunostimulating agent (or mixtures thereof) effective in treating hepatitis virus infection.

The antiviral effectiveness of the aforementioned combinations may involve a variety of different phenomena associated with viral replication and assembly. These may include, for example, blocking hepatitis viral DNA synthesis; blocking viral transcription; blocking virion assembly; blocking virion release or secretion from infected cells; blocking or altering viral protein function, including the function of viral envelope protein(s); and/or the production of immature or otherwise non-functional virions. The overall effect is an inhibition of viral replication and infection of additional cells, and therefore inhibition of the progress of infection in the patient.

N-substituted-1,5-dideoxy-1,5-imino-D-glucose Compounds

N-substituted1,5-dideoxy-1,5-imino-D-glucitol compounds useful in the present invention are represented by structure I below:

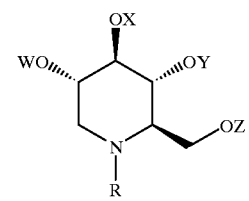

wherein R is selected from arylalkyl, cycloalkylalkyl, and branched or straight chain alkyl having a chain length of $C_1$ to $C_{20}$, preferably $C_2$ to $C_{14}$, more preferably $C_6$ to $C_{12}$. R can also be $C_1$ to $C_{20}$ alkyl, preferably $C_2$ to $C_{14}$, more preferably C6 to $C_{12}$, containing 1 to 5, more preferably 1 to 3, most preferably 1 to 2, oxygen atoms, i.e., oxa derivatives. Preferred R oxa derivatives are 3-oxanonyl, 3-oxadecyl, 7-oxanonyl, and 7-oxadecyl. W, X, Y and Z are independently selected from hydrogen, alkanoyl, aroyl, and trifluoroalkanoyl.

Representative N-substituted-imino-D-glucitol compounds useful in the present invention include, but are not limited to:

N-(n-hexyl-)-1,5-dideoxy1,5-imino-D-glucitol;
N-(n-heptyl-)-1,5-dideoxy-1,5-imino-D-glucitol;
N-(n-octyl-)-1,5-dideoxy-1,5-imino-D-glucitol;
N-(n-octyl-)-1,5-dideoxy-1,5-imino-D-glucitol, tetrabutyrate;
N-(n-nonyl-)-1,5-dideoxy-1,5-imino-D-glucitol, tetrabutyrate;
N-(n-decyl-)-1,5-dideoxy1,5-imino-D-glucitol, tetrabutyrate;

N-(n-undecyl-)-1,5-dideoxy-1,5-imino-D-glucitol, tetrabutyrate;
N-(n-nonyl-)-1,5-dideoxy-1,5-imino-D-glucitol;
N-(n-decyl-)-1,5-dideoxy-,5-imino-D-glucitol;
N-(n-undecyl-)-1,5-dideoxy-1,5-imino-D-glucitol;
N-(n-dodecyl-)-1,5-dideoxy-1,5-imino-D-glucitol;
N-(2-ethylhexyl)-1,5-dideoxy-1,5-imino-D-glucitol;
N-(4-ethylhexyl)-1,5-dideoxy-1,5-imino-D-glucitol;
N-(5-methylhexyl)-1,5-dideoxy-1,5-imino-D-glucitol;
N-(3-propylhexyl)-1,5-dideoxy-1,5-imino-D-glucitol;
N-(1-pentylpentylhexyl)-1,5-dideoxy-1,5-imino-D-glucitol;
N-(1-butylbutyl)-1,5-dideoxy-1,5-imino-D-glucitol;
N-(7-methyloctyl-)-1,5-dideoxy-1,5-imino-D-glucitol;
N-(8-methylnonyl)-1,5-dideoxy-1,5-imino-D-glucitol;
N-(9-methyldecyl)-1,5-dideoxy-1,5-imino-D-glucitol;
N-(10-methylundecyl)-1,5-dideoxy-1,5-imino-D-glucitol;
N-(6-cyclohexylhexyl-)-1,5-dideoxy-1,5-imino-D-glucitol;
N-(4-cyclohexylbutyl)-1,5-dideoxy-1,5-imino-D-glucitol;
N-(2-cyclohexylethyl)-1,5-dideoxy-1,5-imino-D-glucitol;
N-(1-cyclohexylmethyl)-1,5-dideoxy-1,5-imino-D-glucitol;
N-(1-phenylmethyl)-1,5-dideoxy-1,5-imino-D-glucitol;
N-(3-phenylpropyl)-1,5-dideoxy-1,5-imino-D-glucitol;
N-(3-(4-methyl)-phenylpropyl)-1,5-dideoxy-1,5-imino-D-glucitol;
N-(6-phenylhexyl)-1,5-dideoxy-1,5-imino-D-glucitol;
N-(n-nonyl-)-1,5-dideoxy-1,5-imino-D-glucitol, tetrabutyrate;
N-(n-decyl-)-1,5-dideoxy-1,5-imino-D-glucitol, tetrabutyrate;
N-(n-undecyl-)-1,5-dideoxy-1,5-imino-D-glucitol, tetrabutyrate;
N-(n-dodecyl-)-1,5-dideoxy-1,5-imino-D-glucitol, tetrabutyrate;
N-(2-ethylhexyl)-1,5-dideoxy-1,5-imino-D-glucitol, tetrabutyrate;
N-(4-ethylhexyl)-1,5-dideoxy-1,5-imino-D-glucitol, tetrabutyrate;
N-(5-methylhexyl)-1,5-dideoxy-1,5-imino-D-glucitol, tetrabutyrate;
N-(3-propylhexyl)-1,5-dideoxy-1,5-imino-D-glucitol, tetrabutyrate;
N-(1-pentylpentylhexyl)-1,5-dideoxy-1,5-imino-D-glucitol, tetrabutyrate;
N-(1-butylbutyl)-1,5-dideoxy-1,5-imino-D-glucitol, tetrabutyrate;
N-(7-methyloctyl-)-1,5-dideoxy-1,5-imino-D-glucitol, tetrabutyrate;
N-(8-methylnonyl)-1,5-dideoxy-1,5-imino-D-glucitol, tetrabutyrate;
N-(9-methyldecyl)-1,5-dideoxy-1,5-imino-D-glucitol, tetrabutyrate;
N-(10-methylundecyl)-1,5-dideoxy-1,5-imino-D-glucitol, tetrabutyrate;
N-6-cyclohexylhexyl-)-1,5-dideoxy-1,5-imino-D-glucitol, tetrabutyrate;
N-(4-cyclohexylbutyl)-1,5-dideoxy-1,5-imino-D-glucitol, tetrabutyrate;
N-(2-cyclohexylethyl)-1,5-dideoxy-1,5-imino-D-glucitol, tetrabutyrate;
N-(1-cyclohexylmethyl)-1,5-dideoxy-1,5-imino-D-glucitol, tetrabutyrate;
N-(1-phenylmethyl)-1,5-dideoxy-1,5-imino-D-glucitol, tetrabutyrate;
N-(3-phenylpropyl)-1,5-dideoxy-1,5-imino-D-glucitol, tetrabutyrate;
N-(3-(4-methyl)-phenylpropyl)-1,5-dideoxy-1,5-imino-D-glucitol, tetrabutyrate; and
N-(6-phenylhexyl)-1,5-dideoxy-1,5-imino-D-glucitol, tetrabutyrate.

Preferred compounds are N-(n-nonyl-)-1,5-dideoxy-1,5-imino-D-glucitol and N-(n-nonyl-)-1,5-dideoxy-1,5-imino-D-glucitol, tetrabutyrate.

The N-substituted-imino-D-glucitol compounds useful in the present invention can be prepared by methods well known in the art as described in, for example, U.S. Pat. Nos. 4,182,767, 4,639,436, and 5,003,072, as well as PCT International Publication WO 95/19172 and the references cited therein. Methods for introducing oxygen into alkyl side chains are disclosed in Tan et al., (1994) *Glycobiology* 4(2) :141–149. Non-limiting illustrative preparation procedures are presented below in Examples 1 and 2.

In treating hepatitis virus infections, one can use the anti-hepatitis virus combinations or individual compounds of this invention in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

The basic nitrogen-containing groups can be quaternized with agents such as lower alkyl halides, such as methyl, ethyl, propyl, and butyl chloride, bromides, and iodides; dialkyl sulfates such as dimethyl, diethyl, dibuytl, and diamyl sulfates; long chain halides such as decyl, lauryl, myristyl, and stearyl chlorides, bromides, and iodides; aralkyl halides such as benzyl and phenethyl bromides, and others. Water- or oil-soluble or dispersible products are thereby obtained as desired. The salts are formed by combining the basic compounds with the desired acid.

Other compounds of the combinations of this invention that are acids can also form salts. Examples include salts with alkali metals or alkaline earth metals, such as sodium, potassium, calcium, or magnesium, or with organic bases or basic quaternary ammonium salts.

Compounds of the combinations of this invention may be acids or bases. As such, they may be used to form salts with one another. For example, the phosphoric acid form of (−)-2'-deoxy-3'-thiocytidine-5'-triphosphate will form a salt with the base form of N-(n-nonyl)-1,5-dideoxy-1,5-imino-D-glucitol or N-(n-nonyl)-1,5-dideoxy-1,5-imino-D-glucitol, tetrabutyrate. This type of salt can then be provided to the patient in a pharmaceutically acceptable formulation or as a pure single salt.

In some cases, the salts can also be used as an aid in the isolation, purification, or resolution of the compounds of this invention.

Nucleosides and Nucleotides

Nucleosides and nucleotides useful in the present invention are purine (II) base compounds or pyrimidine (III) base compounds, or analogs such as compounds IV or

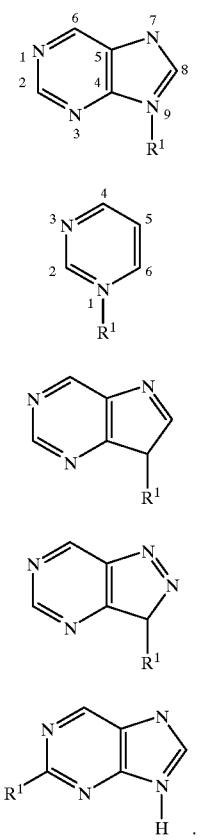

Position numbering for purines and pyrmidines is as shown in structures II and III. R¹ can be selected from hydroxyalkyl, hydroxyalkenyl, thiolalkyl, alkylthioalkyl, alkoxyalkyl, alkoxyalkenyl, heterocycle, heterocycloalkyl, hydroxyalkylalkoxyalkyl, alkoxyalkylalkoxyalkyl, and cycloalkylalkyl. The purine compounds can be further substituted at positions 1, 2, 3, 6, 7, or 8 of the purine heterocycle, and the pyrimidine compounds can be substituted at positions 2, 3, 4, 5, or 6 of the pyrimidine heterocycle. Such substituents can be selected from hydroxy, alkoxy, halo, thiol, amino, mono-substituted amino, di-substituted amino, and alkyl.

When used in combination with another radical when referring to the purines and pyrimidines useful in the present invention, the term "alkyl" means a straight or branched chain hydrocarbon radical containing from 1 to 8 carbon atoms, preferably 1 to 4 carbon atoms. When used in combination with another radical, the term "alkenyl" means a straight or branched chain hydrocarbon radical having 1 or more double bonds, containing from 2 to 8 carbon atoms, preferably 1 to 4 carbon atoms. When used alone when referring to purines and pyrimidines useful in the present invention, the term "alkyl" means a straight or branched chain alkyl radical containing from six to 14 carbon atoms, preferably seven to 12 carbon atoms, and most preferably eight to 11 carbon atoms. The term "aryl" alone or in combination with another radical means a phenyl, naphthyl, or indenyl ring, optionally substituted with one or more substituents selected from alkyl, alkoxy, halogen, hydroxy, or nitro. "Alkanoyl" means branched or straight chain alkanecarbonyl having a chain length of $C_1$ to $C_{20}$ preferably $C_2$ to $C_{14}$, more preferably $C_4$ to $C_{10}$; "aroyl" means arylcarbonyl; and "trifluoroalkanoyl" means alkyl containing three fluoro substituents. "Halogen" means fluorine, chlorine, bromine, or iodine. "Thiol" means sulfur substituted with hydrogen (—SH). "Amino" means nitrogen with two hydrogen atoms; "monosubstituted amino" and "disubstituted amino" mean amino groups further independently substituted with one or more alkyl or arylalkyl groups. "Hydroxyalkyl" means an alkyl group substituted with one or more hydroxyl groups; "hydroxyalkenyl" means an alkenyl group substituted with one or more hydroxyl groups; "thioalkyl" means an alkyl substituted with one or more thiol (SH) groups; "alkoxyalkyl" means an alkyl substituted with one or more alkyl ether groups; "alkoxyalkenyl" means an alkenyl group substituted with one or more alkyl ether groups; "hydroxyalkylalkoxyalkyl" means an alkoxyalkyl group substituted with a hydroxyalkyl group; "alkoxyalkylalkoxyalkyl" means an alkoxyalkyl group substituted with an alkoxyalkyl group; "cycloalkylalkyl" means an alkyl group substituted with a cycloalkyl group. The term "heterocycle," alone or in combination, means a saturated or partially unsaturated 5 or 6-membered ring containing one or more oxygen, nitrogen, and/or sulfur heteroatoms. Said heterocycle can further be substituted with one to four substituents, which can be independently, hydroxy, hydroxyalkyl, thiol, alkoxy, azido, nitro, a halogen atom, amino, mono-substituted amino, or disubstituted amino. Heterocycloalkyl means an alkyl group wherein one or more hydrogen atoms are replaced by a substituted or unsubstituted heterocyclic ring.

Also included are the tautomers of the substituents on the compounds of the invention. Non-limiting examples of tautomers are ketone/enol tautomers, imino/amino tautomers, N-substituted imino/N-substituted amino tautomers, thiol/thiacarbonyl tautomers, and ring-chain tautomers such as the five and six membered ring oxygen, nitrogen, sulfur, or oxygen- and sulfur- containing heterocycles also containing substituents alpha to the heteroatoms. Also specifically included in the present invention are enantiomers and diastereomers, as well as racemates and isomeric mixtures of the compounds discussed herein.

Representative nucleoside and nucleotide compounds useful in the present invention include, but are not limited to:

(+)-cis-5-fluoro-1-[2-(hydroxy-methyl)-[1,3-oxathiolan-5-yl]cytosine;
(−)-2'-deoxy-3'-thiocytidine-5'-triphosphate (3TC);
(−)-cis-5-fluoro-1-[2-(hydroxy-methyl)-[1,3-oxathiolan-5-yl]cytosine (FTC);
(−)2',3', dideoxy-3'-thiacytidine [(−)-SddC];
1-(2'-deoxy-2'-fluoro-beta-D-arabinofuranosyl)-5-iodocytosine (FIAC);
1-(2'-deoxy-2'-fluoro-beta-D-arabinofuranosyl)-5-iodocytosine triphosphate (FIACTP);
1-(2'-deoxy-2'-fluoro-beta-D-arabinofuranosyl)-5-methyluarcil (FMAU);
1-beta-D-ribofuranosyl-1,2,4-triazole-3-carboxamide;
2',3'-dideoxy-3'-fluoro-5-methyl-dexocytidine (FddMeCyt);
2',3'-dideoxy-3'-chloro-5-methyl-dexocytidine (ClddMeCyt);
2',3'-dideoxy-3'-amino-5-methyl-dexocytidine (AddMeCyt);
2',3'-dideoxy-3'-fluoro-5-methyl-cytidine (FddMeCyt);
2',3'-dideoxy-3'-chloro-5-methyl-cytidine (ClddMeCyt);
2',3'-dideoxy-3'-amino-5-methyl-cytidine (AddMeCyt);
2',3'-dideoxy-3'-fluorothymidine (FddThd);
2',3'-dideoxy-beta-L-5-fluorocytidine (beta-L-FddC);
2',3'-dideoxy-beta-L-5-thiacytidine;
2',3'-dideoxy-beta-L-5-cytidine (beta-L-ddC);
2'-deoxy-3'-thia-5-fluorocytosine;
3'-amino-5-methyl-dexocytidine (AddMeCyt);
3'-azido-3'-deoxythymidine (AZT);
3'-chloro-5-methyl-dexocytidine (ClddMeCyt);

9-(2-phosphonyl-methoxyethyl)-2',6'-diaminopurine-2',3'-dideoxyriboside;
9-(2-phosphonylmethoxyethyl)adenine (PMEA);
acyclovir triphosphate (ACVTP);
D-carbocyclic-2'-deoxyguanosine (CdG);
dideoxy-cytidine;
dideoxy-cytosine (ddC);
dideoxy-guanine (ddG);
dideoxy-inosine (ddI);
E-5-(2-bromovinyl)-2'-deoxyuridine triphosphate;
fluoro-arabinofuranosyl-iodouracil;
stavudine;
2-deoxy-3'-thia-5-fluorocytidine;
2',3'-dideoxy-guanine; and
2',3'-dideoxy-guanosine.

A preferred compound is (−)-2'-deoxy-3'-thiocytidine-5'-triphosphate (3TC).

Synthetic methods for the preparation of nucleosides and nucleotides useful in the present invention are likewise well known in the art as disclosed in *Acta Biochim. Pol.*, 43, 25–36 (1996); *Swed. Nucleosides Nucleotides* 15, 361–378 (1996), *Synthesis* 12, 1465–1479 (1995), *Carbohyd. Chem.* 27, 242–276 (1995), *Chem. Nucleosides Nucleotides* 3, 421–535 (1994), Ann. Reports in *Med. Chem.*, Academic Press; and *Exp. Opin. Invest. Drugs* 4, 95–115 (1995).

The chemical reactions described in the references cited above are generally disclosed in terms of their broadest application to the preparation of the compounds of this invention. Occasionally, the reactions may not be applicable as described to each compound included within the scope of compounds disclosed herein. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional will be applicable to the preparation of the corresponding compounds of this invention. In all preparative methods, all starting materials are known or readily preparable from known starting materials.

While nucleoside analogs are generally employed as antiviral agents as is, nucleotides (nucleoside phosphates) must sometimes have to be converted to nucleosides in order to facilitate their transport across cell membranes. An example of a chemically modified nucleotide capable of entering cells is S-1-3-hydroxy-2-phosphonylmethoxypropyl cytosine (HPMPC, Gilead Sciences).

Immunomodulators and Immunostimulants

A large number of immunomodulators and immunostimulants that can be used in the methods of the present invention are currently available. A list of these compounds is provided in Table 1, below.

TABLE 1

| DRUG NAME |
| --- |
| AA-2G |
| adamantylamide dipeptide |
| adenosine deaminase, Enzon |
| adjuvant, Alliance |
| adjuvants, Ribi |
| adjuvants, Vaxcel |

TABLE 1-continued

| DRUG NAME |
| --- |
| Adjuvax |
| agelasphin-11 |
| AIDS therapy, Chiron |
| algal glucan, SRI |
| algammulin, Anutech |
| Anginlyc |
| anticellular factors, Yeda |
| Anticort |
| antigastrin-17 immunogen, Ap |
| antigen delivery system, Vac |
| antigen formulation, IDBC |
| antiGnRH immunogen, Aphton |
| Antiherpin |
| Arbidol |
| Aviron |
| azarole |
| Bay-q-8939 |
| Bay-r-1005 |
| BCH-1393 |
| Betafectin |
| Biostim |
| BL-001 |
| BL-009 |
| Broncostat |
| Cantastim |
| CDRI-84-246 |
| cefodizime |
| chemokine inhibitors, ICOS |
| CMV peptides, City of Hope |
| CN-5888 |
| cytokine-releasing agent, St |
| DHEAS, Paradigm |
| DISC TA-HSV |
| J07B |
| I01A |
| I01Z |
| ditiocarb sodium |
| ECA-10-142 |
| ELS-1 |
| endotoxin, Novartis |
| FCE-20696 |
| FCE-24089 |
| FCE-24578 |
| FLT-3 ligand, Immunex |
| FR-900483 |
| FR-900494 |
| FR-901235 |
| FTS-Zn |
| G-proteins, Cadus |
| gludapcin |
| glutaurine |
| glycophosphopeptical |
| GM-2 |
| GM-53 |
| GMDP |
| growth factor vaccine, EntreM |
| H-BIG, NABI |
| H-CIG, NABI |
| HAB-439 |
| Helicobacter pylori vaccine, |
| herpes-specific immune factor |
| HIV therapy, United Biomed |
| HyperGAM+CF |
| ImmuMax |
| Immun BCG |
| immune therapy, Connective |
| immunomodulator, Evans |
| immunomodulators, Novacell |
| imreg-1 |
| imreg-2 |
| Indomune |
| inosine pranobex |
| interferon, Dong-A (alpha2) |
| interferon, Genentech (gamma) |
| interferon, Novartis (alpha) |
| interleukin-12, Genetics Ins |
| interleukin-15, Immunex |

TABLE 1-continued

| DRUG NAME |
|---|
| interleukin-16, Research Cor |
| ISCAR- 1 |
| J005X |
| L-644257 |
| licomarasminic acid |
| LipoTher |
| LK-409 |
| LK-410 |
| LP-2307 |
| LT (R1926) |
| LW-50020 |
| MAF, Shionogi |
| MDP derivatives, Merck |
| met-enkephalin, TNI |
| methylfurylbutyrolactones |
| MIMP |
| mirimostim |
| mixed bacterial vaccine, Tem |
| MM-1 |
| moniliastat |
| MPLA, Ribi |
| MS-705 |
| murabutide |
| murabutide, Vacsyn |
| muramyl dipeptide derivative |
| muramyl peptide derivatives |
| myelopid |
| N-563 |
| NACOS-6 |
| NH-765 |
| NISV, Proteus |
| NPT-16416 |
| NT-002 |
| PA-485 |
| PEFA-814 |
| peptides, Scios |
| peptidoglycan, Pliva |
| Perthon, Advanced Plant |
| PGM derivative, Pliva |
| Pharmaprojects No. 1099 |
| Pharmaprojects No. 1426 |
| Pharmaprojects No. 1549 |
| Pharmaprojects No. 1585 |
| Pharmaprojects No. 1607 |
| Pharmaprojects No. 1710 |
| Pharmaprojects No. 1779 |
| Pharmaprojects No. 2002 |
| Pharmaprojects No. 2060 |
| Pharmaprojects No. 2795 |
| Pharmaprojects No. 3088 |
| Pharmaprojects No. 3111 |
| Pharmaprojects No. 3345 |
| Pharmaprojects No. 3467 |
| Pharmaprojects No. 3668 |
| Pharmaprojects No. 3998 |
| Pharmaprojects No. 3999 |
| Pharmaprojects No. 4089 |
| Pharmaprojects No. 4188 |
| Pharmaprojects No. 4451 |
| Pharmaprojects No. 4500 |
| Pharmaprojects No. 4689 |
| Pharmaprojects No. 4833 |
| Pharmaprojects No. 494 |
| Pharmaprojects No. 5217 |
| Pharmaprojects No. 530 |
| pidotimod |
| pimelautide |
| pinafide |
| PMD-589 |
| podophyllotoxin, Conpharm |
| POL-509 |
| poly-ICLC |
| poly-ICLC, Yamasa Shoyu |
| PolyA-PolyU |
| Polysaccharide A |
| protein A, Berlox Bioscience |
| PS34WO |

TABLE 1-continued

| DRUG NAME |
|---|
| pseudomonas MAbs, Teijin |
| Psomaglobin |
| PTL-78419 |
| Pyrexol |
| pyriferone |
| Retrogen |
| Retropep |
| RG-003 |
| Rhinostat |
| rifamaxil |
| RM-06 |
| Rollin |
| romurtide |
| RU-40555 |
| RU-41821 |
| rubella antibodies, ResCo |
| S-27609 |
| SB-73 |
| SDZ-280-636 |
| SDZ-MRL-953 |
| SK&F-107647 |
| SL04 |
| SL05 |
| SM-4333 |
| Solutein |
| SRI-62-834 |
| SRL-172 |
| ST-570 |
| ST-789 |
| staphage lysate |
| Stimulon |
| suppressin |
| T-150R1 |
| T-LCEF |
| tabilautide |
| temurtide |
| Theradigm-HBV |
| Theradigm-HPV |
| Theradigm-HSV |
| THF, Pharm & Upjohn |
| THF, Yeda |
| thymalfasin |
| thymic hormone fractions |
| thymocartin |
| thymolymphotropin |
| thymopentin |
| thymopentin analogues |
| thymopentin, Peptech |
| thymosin fraction 5, Alpha |
| thymostimulin |
| thymotrinan |
| TMD-232 |
| TO-115 |
| transfer factor, Viragen |
| tuftsin, Selavo |
| ubenimex |
| Ulsastat |
| ANGG- |
| CD-4+ |
| Collag+ |
| COLSF+ |
| COM+ |
| DA-A+ |
| GAST- |
| GF-TH+ |
| GP-120– |
| IF+ |
| IF-A+ |
| IF-A-2+ |
| IF-B+ |
| IF-G+ |
| IF-G-1B+ |
| JL-2+ |
| IL-12+ |
| IL-15+ |
| IM+ |
| LHRH- |

TABLE 1-continued

DRUG NAME

LIPCOR+
LYM-B+
LYM-NK+
LYM-T+
OPI+
PEP+
PHG-MA+
RNA-SYN–
SY-CW–
TH-A-1+
TH-5+
TNF+
UN

Dosages

The N-substituted-1,5-dideoxy-1,5-imino-D-glucitol compounds useful in the present invention can be administered to humans in an amount in the range of from about 0.1 mg/kg/day to about 100 mg/kg/day, more preferably from about 1 mg/kg/day to about 75 mg/kg/day, and most preferably from about 5 mg/kg/day to about SO mg/kg/day.

The nucleoside or nucleotide antiviral compound, or mixtures thereof, can be administered to humans in an amount in the range of from about 0.1 mg/person/day to about 500 mg/person/day, preferably from about 10 mg/person/day to about 300 mg/person/day, more preferably from about 25 mg/person/day to about 200 mg/person/day, even more preferably from about 50 mg/person/day to about 150 mg/person/day, and most preferably in the range of from about 1 mg/person/day to about 50 mg/person/day.

Immunomodulators and immunostimulants useful in the present invention can be administered in amounts lower than those conventional in the art. For example, thymosin alpha 1 and thymosin fraction 5 are typically administered to humans for the treatment of HepB infections in an amount of about 900 $\mu$g/m$^2$, two times per week (*Hepatology* (1988) 8:1270; *Hepatology* (1989) 10:575; *Hepatology* (1991) 14:409; *Gastroenterology* (1995) 108:A1127). In the methods and compositions of the present invention, this dose can be in the range of from about 10 $\mu$g/m$^2$, two times per week to about 750 $\mu$g/m$^2$, two times per week, more preferably from about 100 $\mu$g/M$^2$, two times per week to about 600 $\mu$g/m$^2$, two times per week, most preferably from about 200 $\mu$g/m$^2$, two times per week to about 400 $\mu$g/m$^2$, two times per week. Interferon alfa is typically administered to humans for the treatment of HepC infections in an amount of from about 1×10$^6$ units/person, three times per week to about 10×10$^6$ units/person, three times per week (Simon et al., (1997) *Hepatology* 25:445–448). In the methods and compositions of the present invention, this dose can be in the range of from about 0.1×10$^6$ units/person, three times per week to about 7.5×10$^6$ units/person, three times per week, more preferably from about 0.5×10$^6$ units/person, three times per week to about 5×10$^6$ units/person, three times per week, most preferably from about 1×10$^6$ units/person, three times per week to about 3×10$^6$ units/person, three times per week.

Due to the enhanced hepatitis virus antiviral effectiveness of these immunomodulators and immunostimulants in the presence of the N-substituted-1,5-dideoxy-1,5-imino-D-glucitol compounds useful in the present invention, reduced amounts of other immunomodulators/immunostimulants can be employed in the methods and compositions disclosed herein. Such reduced amounts can be determined by routine monitoring of hepatitis virus in infected patients undergoing therapy. This can be carried out by, for example, monitoring hepatitis viral DNA in patients' serum by slot-blot, dot-blot, or PCR techniques, or by measurement of hepatitis surface or other antigens, such as the e antigen, in serum. Methods therefor are discussed in Hoofnagle et al., (1997) *New Engl. Jour. Med.* 336(5):347–356, and F. B. Hollinger in *Fields Virology*, Third Ed., Vol. 2 (1996), Bernard N. Fields et al., Eds., Chapter 86, "Hepatitis B Virus," pp. 2738–2807, Lippincott-Raven, Philadelphia, Pa., and the references cited therein.

Patients can be similarly monitored during combination therapy employing N-substituted-1,5-dideoxy-1,5-imino-D-glucitol compounds and nucleoside and/or nucleotide antiviral agents to determine the lowest effective doses of each.

The doses described above can be administered to a patient in a single dose or in proportionate multiple sub-doses. In the latter case, dosage unit compositions can contain such amounts of submultiples thereof to make up the daily dose. Multiple doses per day can also increase the total daily dose should this be desired by the person prescribing the drug.

Pharmaceutical Compositions

The compounds of the present invention can be formulated as pharmaceutical compositions. Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., *Remington's Pharmaceutical Sciences,* Mack Publishing Co., Easton, Pa. (1975), and Liberman, H. A. and Lachman, L., Eds., *Pharmaceutical Dosage Forms*, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form will vary depending upon the patient and the particular mode of administration.

Certain of the pharmaceutical compounds of this invention which are administered in accordance with the methods of the invention can serve as prodrugs to other compounds of this invention. Prodrugs are drugs that can be chemically converted in vivo or in vitro by biological systems into an active derivative or derivatives. Prodrugs are administered in essentially the same fashion as the other pharmaceutical compounds of the invention. Non-limiting examples are the esters of the N-substituted -1,5-dideoxy-1,5-imino-D-glucitol compounds of this invention.

Treatment Regimen

The regimen for treating a patient suffering from a hepatitis virus infection with the compounds and/or compositions of the present invention is selected in accordance with a variety of factors, including the age, weight, sex, diet, and medical condition of the patient, the severity of the infection, the route of administration, pharmacological considerations such as the activity, efficacy, pharmacokinetic, and toxicology profiles of the particular compounds employed, and whether a drug delivery system is utilized.

Administration of the drug combinations disclosed herein should generally be continued over a period of several weeks to several months or years until virus titers reach acceptable levels, indicating that infection has been controlled or eradicated. As noted above, patients undergoing treatment with the drug combinations disclosed herein can be routinely monitored by measuring hepatitis viral DNA in patients' serum by slot-blot, dot-blot, or PCR techniques, or by measurement of hepatitis antigens, such as hepatitis B surface antigen (HBsAg) and hepatitis B e antigen (HBeAg), in serum to determine the effectiveness of therapy. In chronic hepatitis B, for example, remissions are characterized by the disappearance of hepatitis B viral DNA, i.e., reduction to undetectable levels as measured by hybridization tests capable of detecting levels $\geq 10^5$ genomes per ml of serum, and HBeAg from serum despite the continued presence of HBsAg. These serologic events are followed by improvement in the biochemical and histologic features of the disease. The end point of successful treatment in most trials of antiviral therapy is the disappearance of HBeAg and viral DNA from serum. In patients in whom the e antigen disapppears, remission is usually sustained, and results in an inactive HBsAg carrier state. Many patients eventually become HBsAg-negative (see Hoofnagle et al., (1997) New Engl. Jour. Med. 336(5):347–356 for a review).

Continuous analysis of the data obtained by these methods permits modification of the treatment regimen during therapy so that optimal amounts of each component in the combination are administered, and so that the duration of treatment can be determined as well. Thus, the treatment regimen/dosing schedule can be rationally modified over the course of therapy so that the lowest amounts of each of the antiviral compounds used in combination which together exhibit satisfactory anti-hepatitis virus effectiveness are administered, and so that administration of such antiviral compounds in combination is continued only so long as is necessary to successfully treat the infection.

The following non-limiting examples serve to illustrate various aspects of the present invention.

EXAMPLE 1

Preparation of 1,5-(butylimino)-1,5-dideoxy-D-glucitol

A solution of 1,5-dideoxy-1,5-imino-D-glucitol (5.14 g, 0.0315 mole), butyraldehyde (3.35 ml, 0.0380 mole) and Pd black (1 g) in 200 ml methanol was hydrogenated (60 psi/29° C./21 hrs.). After filtering the resulting mixture, the filtrate was concentrated in vacuo to an oil. The title compound was crystallized from acetone, and recrystallized from methanol/acetone, m.p. ca. 132° C. The structure assignment was supported by NMR, infrared spectra and elemental analysis.

Analysis calcd. for $C_{10}H_{21}NO_4$: C, 54.78; H, 9.65; N, 6.39. Found: C, 54.46; H, 9.33; N, 6.46.

EXAMPLE 2

Preparation of 1,5-(butylimino)-1,5-dideoxy-D-glucitol, tetraacetate

Acetic anhydride (1.08 g, 0.0106 mole) was added to the title compound of Example 1 (0.50 g, 0.0023 mole) in 5 ml pyridine and stirred for 17 days at room temperature. The product was evaporated under nitrogen gas. The resulting title compound was purified by silica gel chromatography. Structure assignment was supported by NMR, infrared spectra and elemental analysis.

Analysis calcd. for $C_{18}H_{29}NO_8$: C, 55.80; H, 7.54; N, 3.62. Found: C, 55.42; H, 7.50; N, 3.72.

EXAMPLE 3

Anti-Hepatitis B Virus Activity of (−)-2'-deoxy-3'-thiocytidine-5'-triphosphate (3TC) Alone and in Combination with N-nonyl-DNJ The anti-hepatitis B virus effect of (−)-2'-deoxy-3'-thiocytidine-5'-triphosphate (3TC) alone and in combination with N-nonyl-DNJ was determined according to Korba ((1996) *Antiviral Research* 29(1):49–51), using the "combostat" strategy (Comstat Program, Combostat Corp., Duluth, Minn.). The combostat method involves serially diluting the IC-90 of each compound. The IC-90 of N-nonyl-DNJ has been determined to be between 4 and 10 $\mu$g/ml (T. Block and G. Jacob, unpublished observation). The accepted IC-90 for 3TC in HepG 2.2.15 (2.2.15) cells is 300 nM to 500 nM (Doong et al. (1991) *Proc. Natl. Acad. Sci. USA* 88:8495–8499).

2.2.15 cells, described in Sells et al. (1987) *Proc. Natl. Acad. Sci. USA* 84:1005–1009, were maintained in RPMI 1640 medium (Gibco BRL, #31800-022) supplemented with 10% fetal bovine serum, 200 $\mu$g/ml G418 (Gibco BRL 066-1811). Cells were seeded into 25 $cm^2$ flasks at 80% confluency. Five days later, flasks in triplicate received either no compound, serial dilutions of 3TC alone, or serial dilutions of 3TC plus N-nonyl-DNJ. At 2, 4, and 6 days after addition of compound (with medium replacement on those days), the amount of hepatitis B virus (HBV) DNA in the culture medium was determined by PCR analysis of polyethyleneglycol-sedimented particles. Thus, in these experiments, enveloped particles were not distinguished from nucleocapsids. PCR-amplified products were resolved by agarose gel electrophoresis (1.5% agarose), and the 538 nucleotide fragment was quantified by band scanning (HP Jet Imager). The amount of HBV recovered from untreated cells is assumed to be 100%. Data from the 6-day time point are presented in FIG. 1 as the average values from at least three separate flasks, and the standard error was never greater than 20%, with an average error of 12%.

For each of the three time point series tested, the combination of 3TC plus N-nonyl-DNJ was significantly more effective in inhibiting HBV secretion than either compound alone. Conclusions based upon PCR analysis alone make it difficult to assign precise IC-50 values. The extreme sensitivity and delicate nature of PCR, for example, may account for the inability to achieve greater than 90% inhibition of HBV by 3TC alone, even at 300 nM. Every experiment included controls to assure that PCR was performed in a range of concentrations of DNA in which the reaction yields results proportional to the amount of DNA in the sample. Resolution is approximately 3-fold, i.e., 3-fold differences in DNA concentrations can be detected. The inability to consistently detect less than 3-fold differences probably explains the failure of 3TC alone to achieve 90% inhibition. This suggests that a very high standard of inhibition must be met for the PCR to detect inhibition. Consequently, the trend, over three separate time points, is clear: the combined effect of 3TC plus N-nonyl-DNJ is greater than that of either compound alone, or the additive individual effects of each compound. These data suggest that the IC-50 of 3TC has been moved from about 60 nM to about 0.48 nM when 0.016 $\mu$g/ml N-nonyl-DNJ is present.

EXAMPLE 4

Anti-Hepatitis B Virus Effect of N-nonyl-DNJ Alone in a Woodchuck Model

In order to evaluate the efficacy of N-nonyl-DNJ in combination with 3TC (or other nucleoside or nucleotide analogs) against Hepatitis B virus in a woodchuck animal model, an monotherapy experiment using N-nonyl-DNJ alone was first conducted. This was necessary to determine if N-nonyl-DNJ has any anti-HBV effect in the woodchuck and, if N-nonyl-DNJ has a beneficial effect, to design a combination study based on the dose-response relationship of this drug alone.

Therefore, five groups of four animals each (all groups had both sexes, all but the control had two of each sex) were assigned to 0, 12.5, 25, 50, and 100 mg/kg/day with BID oral dosing. These were lab-reared wild animals. All animals were infected with woodchuck hepatitis virus (WHV) as neonates, and had been tested positive on serological tests for WHV surface antigen. Blood samples were drawn one week prior to dosing (−1 week), immediately before dosing (0 weeks), weekly during dosing (1, 2, 3, and 4 weeks), and after the end of dosing (5, 6, 8, and 10 weeks).

There are two measures of drug efficacy: reduction in total HBV DNA (measured by quantitative PCR), and reduction in HBV DNA from capsids with intact surface glycoproteins, which is the active form of the virus (measured by an ELISA-like immune precipitation assay followed by quantitative PCR). Cell culture experiments with N-nonyl-DNJ demonstrated little or no effect of this compound on total HBV DNA, but a marked effect on the immune precipitated DNA (IPDNA). Not surprisingly, the IPDNA assay is quite variable; as a partial compensation for this, four assay runs were conducted, each containing samples from all animals, but different subsets of the study weeks.

To summarize the results, N-nonyl-DNJ had no effect on total HBV DNA measurements, which were essentially constant for all dose levels over the pre-dose and dosed portions of the study. On the other hand, IPDNA levels were not constant over the study period. The low dose animals tended to have increasing levels of IPDNA over the dosing period (weeks 0–4), while high dose animals tended to have decreasing levels of IPDNA over the same period. Fitting a straight line to each animal's weekly responses gave a significant difference in the slope of these lines due to either dose or plasma level of drug. The plasma levels of drug were also quite variable: animals with the lowest plasma levels in their dose group had lower plasma levels than the animals with the highest plasma levels from the next lower dose group. There were no differences between responses of males and females on any of the measures.

Plasma Levels

Figure 2:
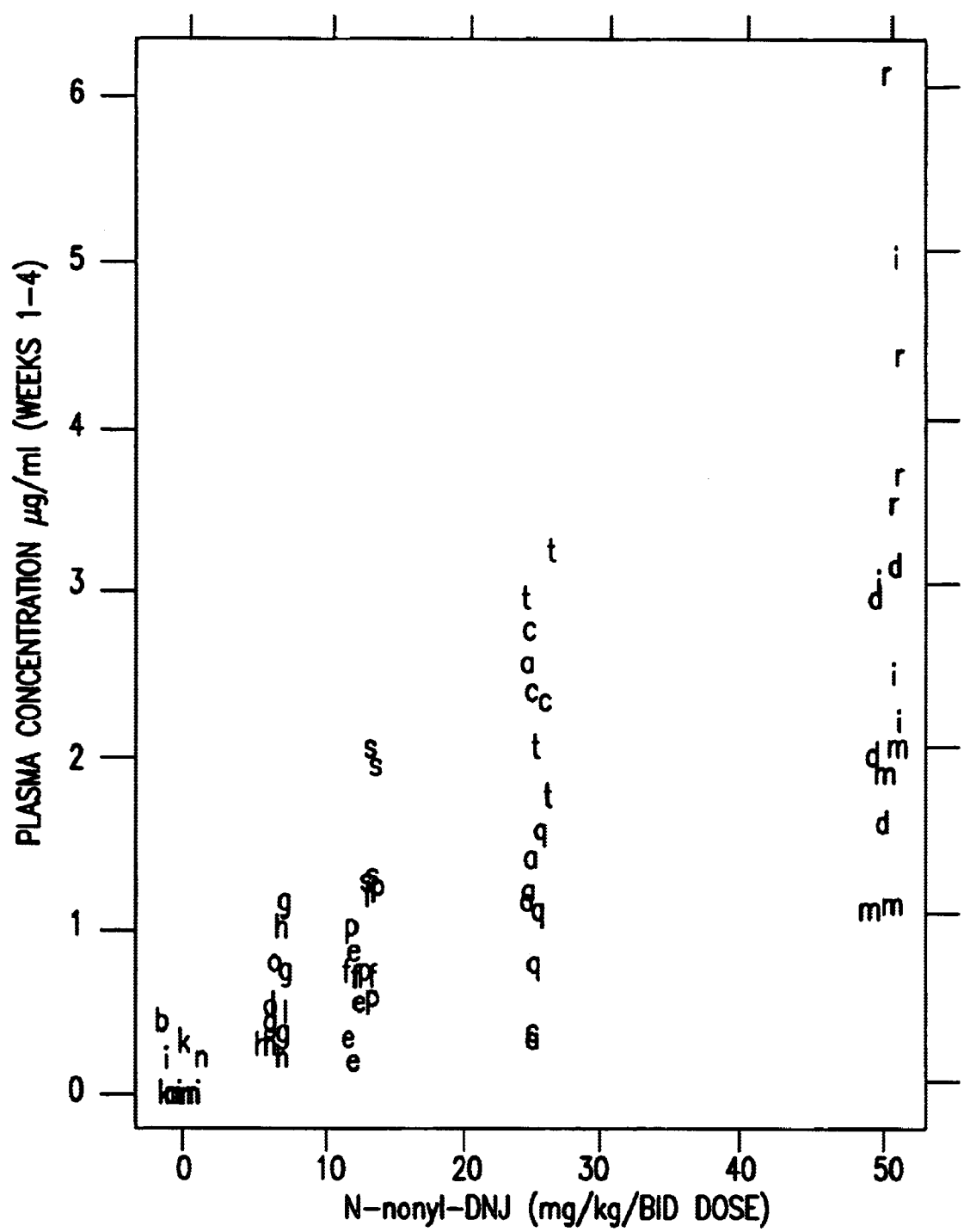
FIG. 2 shows the plasma concentration of N-nonyl-DNJ versus dose of N-nonyl-DNJ for each animal in Example 4, from samples taken during dosing. Animals are indicated by unique letters, and a small amount of random noise has been added to the dose value so that overlapping values can be distinguished.

There were no clear patterns in the changes in plasma levels of N-nonyl-DNJ which could be related to week of dosing or time since previous dose. Because the plasma levels within an animal seemed reasonably consistent during dosing, the median plasma level for each animal was used for subsequent modeling. The plasma levels for each week of the dosing period are plotted for each animal vs. dose (a small amount of random noise is added to the dose level so points which would lie on top of each other on the plot can be distinguished) (FIG. 2).

HBV DNA

The total HBV DNA levels were essentially constant over time within each animal (data not shown). There was a faint hint of a dose-response relationship with decreasing levels of virus with increasing levels of drug, except that three animals at the highest dose had very high virus levels. It is not possible to conclude that there is any relationship between dose of N-nonyl-DNJ and total HBV DNA. It is possible that there are two populations of animals, responders (such as animal r) and non-responders (animals i, m, and d), but more data would be required to permit a firm conclusion on this point.

Immune Precipitated HBV DNA

Substantial variation existed in the IPDNA assay, both between assay runs and within assay runs (data not shown). Even so, it was possible to observe and model a slope over weeks 0–4 which is generally increasing for low dose animals and decreasing for high dose animals. This change in slope was statistically significant ($p<0.005$).

Before models are fitted to the data, a log transform was applied because: 1) the variation in IPDNA increases with increasing IPDNA values; the log transformation gives values with a nearly constant variation, and 2) it is expected that drug effects will appear as a constant multiplier of the IPDNA level. Because there are zero values of IPDNA, a small value (about ½ of the smallest non-zero value) was added to all values before the log transform.

Two approaches were used to model the changes in slope to week with dose of N-nonyl-DNJ: a linear modeling approach and a nonlinear model. Both approaches assume that the (linear) rate of change of the Log(IPDNA) measure over the dosing period is the "right" measure to reflect the effect of the drug on the virus. Both approaches are fit in stages, and the first stage is common to both approaches. First, a simple straight line regression model is fit using weeks 0–4 to predict log(IPDNA+10) separately for each animal by run combination. In the second stage, the response variable is the slope fitted in the first stage.

For the linear approach, a model is fit with slope to week as the response where run is considered a block, dose has a significant effect (almost all of this effect is due to a slope to dose), and the relevant error for testing the effect of dose is the variation among animals treated alike (after the adjustment for the runs as blocks). This is similar to using the calibration data within each run to first adjust each run's data to a common virus DNA concentration; the difference is that here the data from the woodchucks are used for the run adjustment rather than only the calibration data.

For the nonlinear approach, a four parameter logistic model is fit with the slope to week as the response and the dose as the predictor. Again, run is considered a block, but because no run has all weeks, it is not possible to fully reflect the blocking in the nonlinear approach. Even so, the non-linear model yields an EC50 of 7.88 mg/kg/BID dose. The average maximum slope observed was 2.71 additional Log (IPDNA µg/mL)/week, or an increase of about 150%/week, the average minimum slope observed with N-nonyl-DNJ is 0.31 fewer Log(IPDNA µg/mL)/week), or about a decrease of about 25%/week. The slopes, the fitted model, the parameter estimates from the model, and the approximate standard errors for these parameters are all shown in FIG. 3. The data indicate an approximate effective monotherapy dose of N-nonyl-DNJ in woodchucks of about 16 mg/kg/day. Whether in woodchucks or humans, the effective dose of both the N-alkyl-DNJ and nucleoside or nucleotide antiviral agent administered in combination therewith can be administered in two equal daily subdoses (i.e., B.I.D.).

Figure 3:
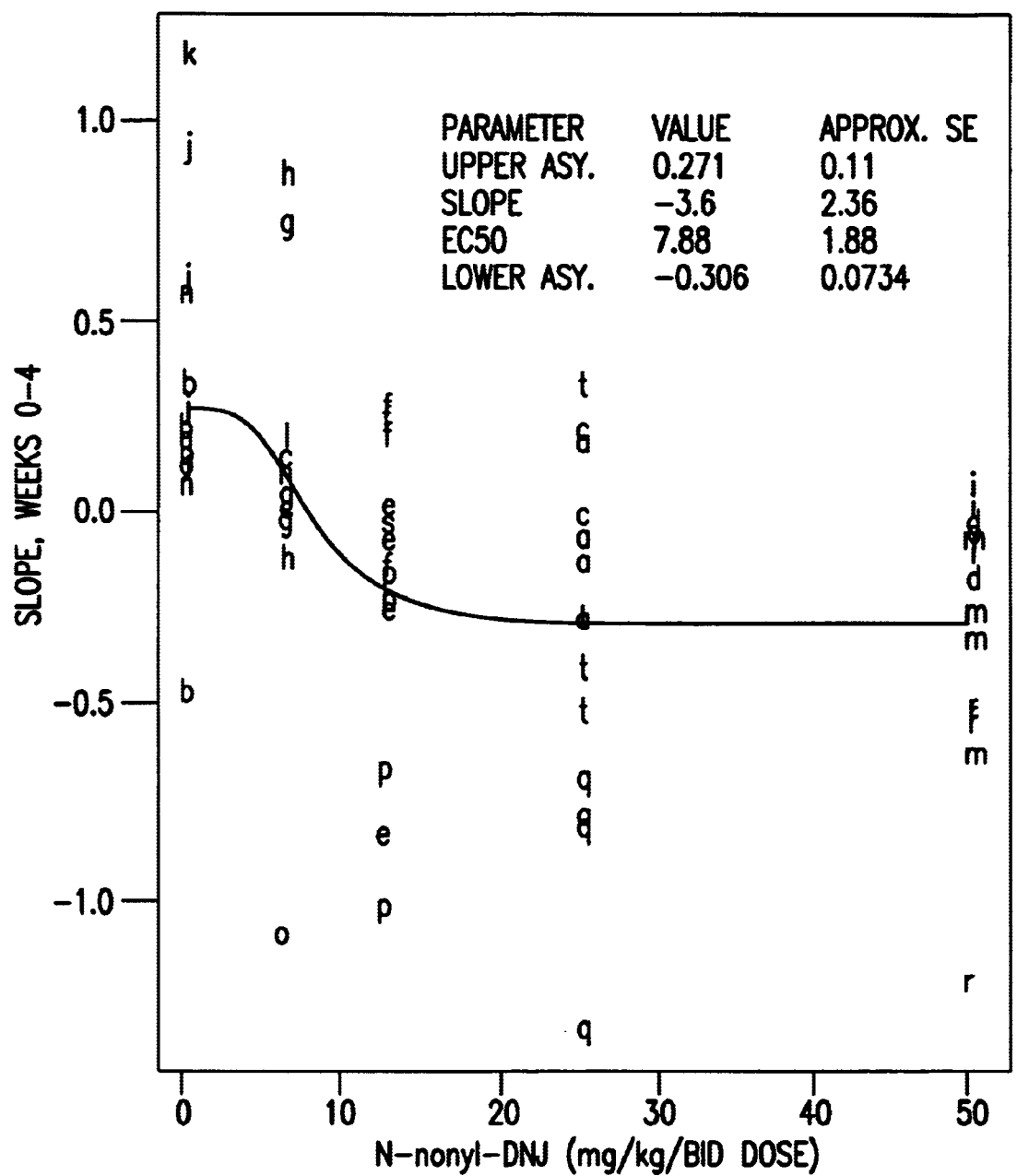
FIG. 3 shows the slope of Log(IPDNA+10) to week versus dose. A distinct letter is used for each animal. The fitted line is from a four parameter logistic model. The parameters of the fitted curve and their approximate standard errors are shown on the plot.

FIGS. 2 and 3 show letters to indicate animals. Table 2 shows two of the animal codes, the sex, and the dose.

TABLE 2

Animal Codes, Sex, and Dose

| Animal Number | Letter Code | Sex | Dose |
|---|---|---|---|
| F95343 | b | F | 0 |
| M96364 | n | M | 0 |
| F96304 | k | F | 0 |
| F96301 | j | F | 0 |
| M96285 | h | M | 6.25 |
| F96283 | g | F | 6.25 |
| F96391 | o | F | 6.25 |
| M96305 | l | M | 6.25 |
| F96271 | f | F | 12.5 |
| M96256 | e | M | 12.5 |
| M96404 | s | M | 12.5 |
| F96392 | p | F | 12.5 |
| F96163 | c | F | 25 |
| M96414 | t | M | 25 |
| F96393 | q | F | 25 |
| M95322 | a | M | 25 |
| M96286 | i | M | 50 |
| F96231 | d | F | 50 |
| F96402 | r | F | 50 |
| M96363 | m | M | 50 |

EXAMPLE 5

Antiviral Study to Test the Activity of N-nonyl-DNJ in Combination with 3TC in a Woodchuck Model of Hepatitis B Virus Infection The combined activity of N-nonyl-DNJ and the nucleoside analog 3TC can be assessed using the woodchuck model of hepatitis B virus infection. Twenty-eight woodchucks with persistent woodchuck hepatitis virus (WHV) infection can be utilized. Groups of woodchucks can be treated orally with 3TC alone (s.i.d.), with N-nonyl-DNJ alone (b.i.d.), or with combinations of the two drugs. The antiviral activity of the individual drugs and combinations can be assessed by measuring serum WHV DNA during treatment, and comparing the results of treated groups to placebo treated controls.

Twenty-eight woodchucks with established persistent WHV infection can be used, all of which were experimentally infected with WHV during the first week of life. All can be WHsAg positive at the time the study is initiated.

A total of eight experimental groups can be used. Woodchucks in each group can be stratified on the basis of gender, body weight, and age. 3TC can be administered orally as an aqueous suspension of Epivir (Glaxo-Wellcome) tablets one time per day. N-nonyl-DNJ can also be administered orally in aqueous solution, in two divided doses. Treatment with both drugs can be followed by the administration of 4 to 5 mls of semisynthetic liquid woodchuck diet to insure complete ingestion of the drugs.

The experimental groups can be as follows:

| Group ID | No. | 3TC (mg/kg/day) | N-nonyl-DNJ (mg/kg/day) |
|---|---|---|---|
| 1 | 4 | 0.0 | 0.0 |
| 2 | 3 | 3.0 | 0.0 |
| 3 | 3 | 9.0 | 0.0 |
| 4 | 3 | 0.0 | 4.0 |
| 5 | 3 | 0.0 | 12.0 |
| 6 | 4 | 1.5 | 2.0 |

-continued

| Group ID | No. | 3TC (mg/kg/day) | N-nonyl-DNJ (mg/kg/day) |
|---|---|---|---|
| 7 | 4 | 4.5 | 6.0 |
| 8 | 4 | 9.0 | 12.0 |

Woodchucks can be anesthetized (50 mg/kg ketamine, 5 mg/kg zylazine), weighed, and blood samples obtained prior to initial treatment, at weekly intervals during the six week period of treatment, and at 1, 2, and 4 weeks following treatment. Serum can be harvested and divided into aliquots. One aliquot can be used for analysis of WHV DNA by dot blot hybridization and for WHsAg by ELISA. CBCs and clinical biochemical profiles can be obtained prior to treatment and at the end of treatment. A second aliquot can be maintained as an archive sample. Other aliquots of serum can be used for drug analysis and special WHV DNA analyses.

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A method of treating a hepatitis virus infection in a mammal, comprising administering to said mammal a first amount of an N-substituted-1,5-dideoxy-1,5-imino-D-glucitol compound of Formula I or a pharmaceutically acceptable salt thereof:

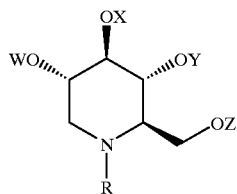

I wherein:
R is selected from the group consisting of arylalkyl, cycloalkylalkyl, and branched or straight chain alkyl having a chain length of $C_1$ to $C_{20}$, and
W, X, Y, and Z are each independently selected from the group consisting of hydrogen, alkanoyl, aroyl, and trifluoroalkanoyl; and
a second amount of an antiviral compound selected from the group consisting of a nucleoside antiviral compound, a nucleotide antiviral compound, and mixtures thereof,
wherein said first and second amounts of said compounds together comprise an anti-hepatitis virus effective amount of said compounds.

2. The method of claim 1, wherein R is a branched or straight chain alkyl having a chain length of $C_1$ to $C_{20}$, and W, X, Y, and Z are each hydrogen.

3. The method of claim 2, wherein R is a straight chain alkyl having a chain length of $C_1$ to $C_{20}$.

4. The method of claim 3, wherein R is a straight chain alkyl having a chain length of $C_2$ to $C_{14}$.

5. The method of claim 4, wherein R is a straight chain alkyl having a chain length of $C_6$ to $C_{12}$.

6. The method of claim 5, wherein R is nonyl.

7. The method of claim 1, wherein R is a branched or straight chain alkyl having a chain length of $C_1$ to $C_{20}$, and W, X, Y, and Z are each alkanoyl.

8. The method of claim 7 wherein R is a straight chain alkyl having a chain length of $C_1$ to $C_{20}$.

9. The method of claim 8, wherein R is a straight chain alkyl having a chain length of $C_2$ to $C_{14}$.

10. The method of claim 9, wherein R is a straight chain alkyl having a chain length of $C_6$ to $C_{12}$.

11. The method of claim 10, wherein R is nonyl.

12. The method of claim 7, wherein said alkanoyl has a chain length of $C_1$ to $C_{20}$.

13. The method of claim 7, wherein said alkanoyl has a chain length of $C_2$ to $C_{14}$.

14. The method of claim 7, wherein said alkanoyl has a chain length of $C_3$ to $C_{10}$.

15. The method of claim 7, wherein said alkanoyl is butanoyl.

16. The method of claim 7, wherein R is nonyl and W, X, Y, and Z are each butanoyl.

17. The method of claim 1, wherein
R is a straight chain alkyl having a chain length of $C_1$ to $C_{20}$,
W, X, Y, and Z are each hydrogen, and
said antiviral compound is a nucleoside antiviral compound.

18. The method of claim 1, wherein
R is a straight chain alkyl having a chain length of $C_1$ to $C_{20}$,
W, x, Y, and Z are each butanoyl, and
said antiviral compound is a nucleoside antiviral compound.

19. The method of claim 1, wherein said N-substituted-1,5-dideoxy-1,5-imino-D-glucitol compound is selected from the group consisting of:
N-(n-hexyl-)-1,5-dideoxy-1,5-imino-D-glucitol;
N-(n-heptyl-)-1,5-dideoxy-1,5-imino-D-glucitol;
N-(n-octyl-)-1,5-dideoxy-1,5-imino-D-glucitol;
N-(n-octyl-)-1,5-dideoxy-1,5-imino-D-glucitol, tetrabutyrate;
N-(n-nonyl-)-1,5-dideoxy-1,5-imino-D-glucitol, tetrabutyrate;
N-(n-decyl-)-1,5-dideoxy-1,5-imino-D-glucitol, tetrabutyrate;
N-(n-undecyl-)-1,5-dideoxy-1,5-imino-D-glucitol, tetrabutyrate;
N-(n-nonyl-)-1,5-dideoxy-1,5-imino-D-glucitol;
N-(n-decyl-)-1,5-dideoxy-1,5-imino-D-glucitol;
N-(n-undecyl-)-1,5-dideoxy-1,5-imino-D-glucitol;
N-(n-dodecyl-)-1,5-dideoxy-1,5-imino-D-glucitol;
N-(2-ethylhexyl)-1,5-dideoxy-1,5-imino-D-glucitol;
N-(4-ethylhexyl)-1,5-dideoxy-1,5-imino-D-glucitol;
N-(5-methylhexyl)-1,5-dideoxy-1,5-imino-D-glucitol;
N-(3-propylhexyl)-1,5-dideoxy-1,5-imino-D-glucitol;
N-(1-pentylpentylhexyl)-1,5-dideoxy-1,5-imino-D-glucitol;
N-(1-butylbutyl)-1,5-dideoxy-1,5-imino-D-glucitol;
N-(7-methyloctyl-)-1,5-dideoxy-1,5-imino-D-glucitol;
N-(8-methylnonyl)-1,5-dideoxy-1,5-imino-D-glucitol;
N-(9-methyldecyl)-1,5-dideoxy-1,5-imino-D-glucitol;
N-(10-methylundecyl)-1,5-dideoxy-1,5-imino-D-glucitol;

N-(6-cyclohexylhexyl-)-1,5-dideoxy-1,5-imino-D-glucitol;
N-(4-cyclohexylbutyl)-1,5-dideoxy-1,5-imino-D-glucitol;
N-(2-cyclohexylethyl)-1,5-dideoxy-1,5-imino-D-glucitol;
N-(2-cyclohexylmethyl)-1,5-dideoxy-1,5-imino-D-glucitol;
N-(1-phenylmethyl)-1,5-dideoxy-1,5-imino-D-glucitol;
N-(3-phenylpropyl)-1,5-dideoxy-1,5-imino-D-glucitol;
N-(3-(4-methyl)-phenylpropyl)-1,5-dideoxy-1,5-imino-D-glucitol;
N-(6-phenylhexyl)-1,5-dideoxy-1,5-imino-D-glucitol;
N-(n-nonyl-)-1,5-dideoxy-1,5-imino-D-glucitol, tetrabutyrate;
N-(n-decyl-)-1,5-dideoxy-1,5-imino-D-glucitol, tetrabutyrate;
N-(n-undecyl-)-1,5-dideoxy-1,5-imino-D-glucitol, tetrabutyrate;
N-(n-dodecyl-)-1,5-dideoxy-1,5-imino-D-glucitol, tetrabutyrate;
N-(2-ethylhexyl)-1,5-dideoxy-1,5-imino-D-glucitol, tetrabutyrate;
N-(4-ethylhexyl)-1,5-dideoxy-1,5-imino-D-glucitol, tetrabutyrate;
N-(5-methylhexyl)-1,5-dideoxy-1,5-imino-D-glucitol, tetrabutyrate;
N-(3-propylhexyl)-1,5-dideoxy-1,5-imino-D-glucitol, tetrabutyrate;
N-(1-pentylpentylhexyl)-1,5-dideoxy-1,5-imino-D-glucitol, tetrabutyrate;
N-(1-butylbutyl)-1,5-dideoxy-1,5-imino-D-glucitol, tetrabutyrate;
N-(7-methyloctyl-)-1,5-dideoxy-1,5-imino-D-glucitol, tetrabutyrate;
N-(8-methylnonyl)-1,5-dideoxy-1,5-imino-D-glucitol, tetrabutyrate;
N-(9-methyldecyl)-1,5-dideoxy-1,5-imino-D-glucitol, tetrabutyrate;
N-(10-methylundecyl)-1,5-dideoxy-1,5-imino-D-glucitol, tetrabutyrate;
N-(6-cyclohexylhexyl-)-1,5-dideoxy-1,5-imino-D-glucitol, tetrabutyrate;
N-(4-cyclohexylbutyl)-1,5-dideoxy-1,5-imino-D-glucitol, tetrabutyrate;
N-(2-cyclohexylethyl)-1,5-dideoxy-1,5-imino-D-glucitol, tetrabutyrate;
N-(1-cyclohexylmethyl)-1,5-dideoxy-1,5-imino-D-glucitol, tetrabutyrate;
N-(1-phenylmethyl)-1,5-dideoxy-1,5-imino-D-glucitol, tetrabutyrate;
N-(3-phenylpropyl)-1,5-dideoxy-1,5-imino-D-glucitol, tetrabutyrate;
N-(3-(4-methyl)-phenylpropyl)-1,5-dideoxy-1,5-imino-D-glucitol, tetrabutyrate; and
N-(6-phenylhexyl)-1,5-dideoxy-1,5-imino-D-glucitol, tetrabutyrate, and
said nucleoside or nucleotide antiviral compound is selected from the group consisting of:
(+)-cis-5-fluoro-1-[2-(hydroxy-methyl)-[1,3-oxathiolan-5-yl]cytosine;
(−)-2'-deoxy-3'-thiocytidine-5'-triphosphate (3TC);
(−)-cis-5-fluoro-1-[2-(hydroxy-methyl)-[1,3-oxathiolan-5-yl]cytosine (FTC);
(−)2',3', dideoxy-3'-thiacytidine [(−)-SddC];
1-(2'-deoxy-2'-fluoro-beta-D-arabinofuranosyl)-5-iodocytosine (FIAC);
1-(2'-deoxy-2'-fluoro-beta-D-arabinofuranosyl)-5-iodocytosine triphosphate (FIACTP);
1-(2'-deoxy-2'-fluoro-beta-D-arabinofuranosyl)-5-methyluarcil (FMAU);
1-beta-D-ribofuranosyl-1,2,4-triazole-3-carboxamide;
2',3'-dideoxy-3'-fluoro-5-methyl-dexocytidine (FddMeCyt);
2',3'-dideoxy-3'-chloro-5-methyl-dexocytidine (ClddMeCyt);
2',3'-dideoxy-3'-amino-5-methyl-dexocytidine (AddMeCyt);
2',3'-dideoxy-3'-fluoro-5-methyl-cytidine (FddMeCyt);
2',3'-dideoxy-3'-chloro-5-methyl-cytidine (ClddMeCyt);
2',3'-dideoxy-3'-amino-5-methyl-cytidine (AddMeCyt);
2',3'-dideoxy-3'-fluorothymidine (FddThd);
2',3'-dideoxy-beta-L-5-fluorocytidine (beta-L-FddC);
2',3'-dideoxy-beta-L-5-thiacytidine;
2',3'-dideoxy-beta-L-5-cytidine (beta-L-ddc);
2',3-deoxy-3'-thia-5-fluorocytosine;
3'-amino-5-methyl-dexocytidine (AddMeCyt);
3'-azido-3'-deoxythymidine (AZT);
3'-chloro-5-methyl-dexocytidine (ClddMeCyt);
9-(2-phosphonyl-methoxyethyl)-2',6'-diaminopurine-2',3'-dideoxyriboside;
9-(2-phosphonylmethoxyethyl)adenine (PMEA);
acyclovir triphosphate (ACVTP);
D-carbocyclic-2'-deoxyguanosine (CdG);
dideoxy-cytidine;
dideoxy-cytosine (ddC);
dideoxy-guanine (ddG);
dideoxy-inosine (ddI);
E-5-(2-bromovinyl)-2'-deoxyuridine triphosphate;
fluoro-arabinofuranosyl-iodouracil;
stavudine;
2-deoxy-3'-thia-5-fluorocytidine;
2',3'-dideoxy-guanine; and
2',3'-dideoxy-guanosine.

20. The method of claim 1, wherein said N-substituted-1,5-dideoxy-1,5-imino-D-glucitol compound is selected from the group consisting of N-(n-nonyl)-1,5-dideoxy-1,5-imino-D-glucitol and N-(n-nonyl)-1,5-dideoxy-1,5-imino-D-glucitol, tetrabutyrate, and said nucleoside antiviral compound is (−)-2'-deoxy-3'-thiocytidine-5'-triphosphate (3TC).

21. The method of claim 20, wherein said N-substituted-1,5-dideoxy-1,5-imino-D-glucitol compound is N-(n-nonyl)-1,5-dideoxy-1,5-imino-D-glucitol and said nucleoside antiviral compound is (−)-2'-deoxy-3'-thiocytidine-5'-triphosphate (3TC).

22. The method of claim 1, wherein said first amount of said N-substituted-1,5-dideoxy-1,5-imino-D-glucitol compound is in the range of from about 0.1 mg/kg/day to about 100 mg/kg/day.

23. The method of claim 22, wherein said first amount of said N-substituted-1,5-dideoxy-1,5-imino-D-glucitol compound is in the range of from about 1 mg/kg/day to about 75 mg/kg/day.

24. The method of claim 23, wherein said first amount of said N-substituted-1,5-dideoxy-1,5-imino-D-glucitol compound is in the range of from about 5 mg/kg/day to about 50 mg/kg/day.

25. The method of claim 1, wherein said second amount of said nucleoside or nucleotide antiviral compound, or mixture thereof, is in the range of from about 0.1 mg/person/day to about 500 mg/person/day.

26. The method of claim 25, wherein said second amount of said nucleoside or nucleotide antiviral compound, or mixture thereof, is in the range of from about 10 mg/person/day to about 300 mg/person/day.

27. The method of claim 26, wherein said second amount of said nucleoside or nucleotide antiviral compound, or mixture thereof, is in the range of from about 25 mg/person/day to about 200 mg/person/day.

28. The method of claim 27, wherein said second amount of said nucleoside or nucleotide antiviral compound, or mixture thereof, is in the range of from about 50 mg/person/day to about 150 mg/person/day.

29. The method of claim 1, wherein said second amount of said nucleoside or nucleotide antiviral compound, or mixture thereof, is in the range of from about 1 mg/person/day to about 50 mg/person/day.

30. The method of claim 1, wherein said hepatitis virus infection is a hepatitis B virus infection.

31. A method of treating a hepatitis B virus infection in a mammal, comprising administering to said mammal from about 0.1 mg/kg/day to about 100 mg/kg/day of an N-substituted-1,5-dideoxy-1,5-imino-D-glucitol compound of Formula I:

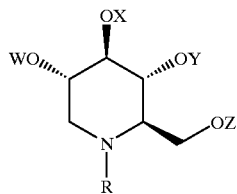

wherein:
R is selected from the group consisting of arylalkyl, cycloalkylalkyl, and branched or straight chain alkyl having a chain length of $C_1$ to $C_{20}$, and
W, X, Y, and Z are each independently selected from the group consisting of hydrogen, alkanoyl, aroyl, and trifluoroalkanoyl; and
from about 0.1 mg/person/day to about 500 mg/person/day of a compound selected from the group consisting of a nucleoside antiviral compound, a nucleotide antiviral, and mixtures thereof.

32. The method of claim 31, wherein said N-substituted-1,5-dideoxy-1,5-imino-D-glucitol compound is selected from the group consisting of N-(n-nonyl-)-1,5-dideoxy-1,5-imino-D-glucitol and N-(n-nonyl-)-1,5-dideoxy-1,5-imino-D-glucitol, tetrabutyrate, and said nucleoside antiviral agent is (−)-2'-deoxy-3'-thiocytidine-5'-triphosphate (3TC).

33. The method of claim 32, wherein said N-substituted-1,5-dideoxy-1,5-imino-D-glucitol compound is N-(n-nonyl-)-1,5-dideoxy-1,5-imino-D-glucitol.

34. A method of treating a hepatitis B virus infection in a human patient, comprising administering to said human patient from about 0.1 mg/kg/day to about 100 mg/kg/day of N-(n-nonyl-)-1,5dideoxy-1,5-imino-D-glucitol and from about 0.1 mg/person/day to about 500 mg/person/day of (−)-2'-deoxy-3'-thiocytidine-5'-triphosphate.

35. A method of treating a hepatits virus infection in a mammal, comprising administering to said mammal a first amount of an N-substituted,-1,5-dideoxy-1,5-imino-D-glucitol compound of Formula I or a pharmaceutically acceptable salt thereof:

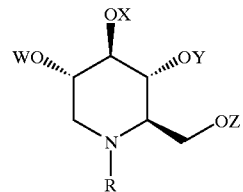

wherein:
R is branched or straight chain alkyl having a chain length of $C_6$ to $C_{12}$; and
W, X, Y, and Z are each independently selected from the group consisting of hydrogen, alkanoyl, aroyl, and trifluoroalkanoyl; and
a second amount of an antiviral compound selected from the group consisting of a nucleoside antiviral compound, a nucleotide antiviral compound, and mixtures thereof;
wherein said first and second amounts of said compounds together comprise an anti-hepatitis virus effective amount of said compounds.

36. The method of claim 35 wherein W, X, Y, and Z are each hydrogen; and wherein said nucleoside or nucleotide antiviral compound is selected from the group consisting of:

(+)-cis-5-fluoro-1-[2-(hydroxy-methyl)-[1,3oxathiolan-5-yl]cytosine;
(-)-2'-deoxy-3'-thiocytidine-5'-triphosphate (3TC);
(-)-cis-5-fluoro-1-[2-(hydroxy-methyl)-[1,3-oxathiolan-5- yl]cytosine (FTC);
(-)2',3', dideoxy-3'-thiacytidine [(-)-SddC];
1-2'-deoxy-2'-fluoro-beta-D-arabinofuranosyl)-5- iodocytosine (FIAC);
1-(2'-deoxy-2'-fluoro-beta-D-arabinofuranosyl)-5-iodocytosine triphosphate (FIACTP);
1-(2'-deoxy-2'-fluoro-beta-D-arabinofuranosyl)-5-methyluarcil (FMAU);
1-beta-D-ribofuranosyl-1,2,4,-triazole-3-carboxamide;
2',3'-dideoxy-3'-fluoro-5-methyl-dexocytidine (FddMeCyt);
2',3'-dideoxy-3'-chloro-5-methyl-dexocytidine (ClddMeCyt);
2',3'-dideoxy-3'-amino-5-methyl-dexocytidine (AddMeCyt);
2',3'-dideoxy-3'-fluoro-5-methyl-cytidine (FddMeCyt);
2',3'-dideoxy-3'-chloro-5-methyl-cytidine (ClddMeCyt);
2',3'-dideoxy-3'-amino-5-methyl-cytidine (AddMeCyt);
2',3'-dideoxy-3'-fluorothymidine (FddThd);
2',3'-dideoxy-beta-L-5-fluorocytidine (beta-L-FddC);
2',3'-dideoxy-beta-L-5-thiacytidine;
2',3'-dideoxy-beta-L-5-cytidine (beta-L-ddC);
2'-deoxy-3'-thia-5-fluorocytosine;
3'-amino-5-methyl-dexocytidine (AddMeCyt);
3'-azido-3'-deoxythymidine (AZT);
3'-chloro-5-methyl-dexocytidine (ClddMeCyt);
9- (2-phosphonyl-methoxyethyl)-2',6'-diaminopurine-2',3'- dideoxyriboside;
9- (2-phosphonylmethoxyethyl) adenine (PMEA);
acyclovir triphosphate (ACVTP);

D-carbocyclic-2'-deoxyguanosine (CdG);
dideoxy-cytidine;
dideoxy-cytosine (ddC);
dideoxy-guanine (ddG);
dideoxy-inosine (ddI);
E-5- (2-bromovinyl)-2'-deoxyuridine triphosphate;
fluoro-arabinofuranosyl-iodouracil;
stavudine;
2-deoxy-3'-thia-5-fluorocytidine;
2',3'-dideoxy-guanine; and
2',3'-dideoxy-guanosine.

37. The method of claim 36 wherein said nucleoside antiviral compound is (-)-2'-deoxy-3'-thiocytidine-5'- triphosphate (3TC).

38. The method of claim 35 wherein W, X, Y, and Z are each alkanoyl; and wherein said nucleoside or nucleotide antiviral compound is selected from the group consisting of:
  (+)-cis-5-fluoro-1-[2-(hydroxy-methyl)-[1,3-oxathiolan-5- yl]cytosine;
  (-)-2'-deoxy-3'-thiocytidine-5'-triphosphate (3TC);
  (-)-cis-5-fluoro-1-[2-(hydroxy-methyl)-[1,3-oxathiolan-5-yl]cytosine (FTC);
  (-)2',3', dideoxy-3'-thiacytidine [(-)-SddC];
  1-2'-deoxy-2'-fluoro-beta-D-arabinofuranosyl)-5- iodocytosine (FIAC);
  1-(2'-deoxy-2'-fluoro-beta-D-arabinofuranosyl)-5-iodocytosine triphosphate (FIACTP);
  1-(2'-deoxy-2'-fluoro-beta-D-arabinofuranosyl)-5-methyluarcil (FMAU);
  1-beta-D-ribofuranosyl-1,2,4,-triazole-3-carboxamide;
  2',3'-dideoxy-3'-fluoro-5-methyl-dexocytidine (FddMeCyt);
  2',3'-dideoxy-3'-chloro-5-methyl-dexocytidine (ClddMeCyt);
  2',3'-dideoxy-3'-amino-5-methyl-dexocytidine (AddMeCyt);
  2',3'-dideoxy-3'-fluoro-5-methyl-cytidine (FddMeCyt);
  2',3'-dideoxy-3'-chloro-5-methyl-cytidine (ClddMeCyt);
  2',3'-dideoxy-3'-amino-5-methyl-cytidine (AddMeCyt);
  2',3'-dideoxy-3'-fluorothymidine (FddThd);
  2',3'-dideoxy-beta-L-5-fluorocytidine (beta-L-FddC);
  2',3'-dideoxy-beta-L-5-thiacytidine;
  2',3'-dideoxy-beta-L-5-cytidine (beta-L-ddC);
  2'-deoxy-3'-thia-5-fluorocytosine;
  3'-amino-5methyl-dexocytidine (AddMeCyt);
  3'-azido-3'-deoxythymidine (AZT);
  3'-chloro-5-methyl-dexocytidine (ClddMeCyt);
  9- (2-phosphonyl-methoxyethyl)-2',6'-diaminopurine-2',3'- dideoxyriboside;
  9- (2-phosphonylmethoxyethyl) adenine (PMEA);
  acyclovir triphosphate (ACVTP);
  D-carbocyclic-2'-deoxyguanosine (CdG);
  dideoxy-cytidine;
  dideoxy-cytosine (ddC);
  dideoxy-guanine (ddG);
  dideoxy-inosine (ddI);
  E-5- (2-bromovinyl)-2'-deoxyuridine triphosphate;
  fluoro-arabinofuranosyl-iodouracil;
  stavudine;
  2-deoxy-3'-thia-5-fluorocytidine;
  2',3'-dideoxy-guanine; and
  2',3'-dideoxy-guanosine.

39. The method fo claim 38 wherein said nucleoside antiviral compound is (-)-2'-deoxy-3'-thiocytidine-5'- triphosphate (3TC).

40. The method of claim 39 wherein W, X, Y, and Z are each butanoyl.

41. The method of claim 35, wherein said first amount of said N-substituted-1,5-dideoxy-1,5-imino-D-glucitol compound is in the range of from about 0.1 mg to about 100 mg/kg/day, and wherein said second amount of said nucleoside or nucleotide antiviral compound, or mixture thereof, is in the range of from about 0.1 mg/person/day to about 500 mg/person/day.

42. The method fo claim 35 wherein said hepatitis virus infection is a hepatitis B virus infection.

43. The method of claim 42 wherein W, X, Y, and Z are each alkanoyl; and wherein said nucleoside or nucleotide antiviral compound is selected from the group consisting of:
  (+)-cis-5-fluoro-1-[2-(hydroxy-methyl)-[1,3-oxathiolan-5-yl]cytosine;
  (-)-2'-deoxy-3'-thiocytidine-5'-triphosphate (3TC);
  (-)-cis-5-fluoro-1-[2-(hydroxy-methyl)-[1,3-oxathiolan-5- yl]cytosine (FTC);
  (-)2',3', dideoxy-3'-thiacytidine [(-)-SddC];
  1-2'-deoxy-2'-fluoro-beta-D-arabinofuranosyl)-5- iodocytosine (FIAC);
  1-(2'-deoxy-2'-fluoro-beta-D-arabinofuranosyl)-5-iodocytosine triphosphate (FIACTP);
  1-(2'-deoxy-2'-fluoro-beta-D-arabinofuranosyl)-5-methyluarcil (FMAU);
  1-beta-D-ribofuranosyl-1,2,4,-triazole-3-carboxamide;
  2',3'-dideoxy-3'-fluoro-5-methyl-dexocytidine (FddMeCyt);
  2',3'-dideoxy-3'-chloro-5-methyl-dexocytidine (ClddMeCyt);
  2',3'-dideoxy-3'-amino-5-methyl-dexocytidine (AddMeCyt);
  2',3'-dideoxy-3'-fluoro-5-methyl-cytidine (FddMeCyt);
  2',3'-dideoxy-3'-chloro-5-methyl-cytidine (ClddMeCyt);
  2',3'-dideoxy-3'-amino-5-methyl-cytidine (AddMeCyt);
  2',3'-dideoxy-3'-fluorothymidine (FddThd);
  2',3'-dideoxy-beta-L-5-fluorocytidine (beta-L-FddC);
  2',3'-dideoxy-beta-L-5-thiacytidine;
  2',3'-dideoxy-beta-L-5-cytidine (beta-L-ddC);
  2'-deoxy-3'-thia-5-fluorocytosine;
  3'-amino-5methyl-dexocytidine (AddMeCyt);
  3'-azido-3'-deoxythymidine (AZT);
  3'-chloro-5-methyl-dexocytidine (ClddMeCyt);
  9- (2-phosphonyl-methoxyethyl)-2',6'-diaminopurine-2',3'- dideoxyriboside;
  9- (2-phosphonylmethoxyethyl) adenine (PMEA);
  acyclovir triphosphate (ACVTP);
  D-carbocyclic-2'-deoxyguanosine (CdG);
  dideoxy-cytidine;
  dideoxy-cytosine (ddC);
  dideoxy-guanine (ddG);
  dideoxy-inosine (ddI);
  E-5- (2-bromovinyl)-2'-deoxyuridine triphosphate;
  fluoro-arabinofuranosyl-iodouracil;

stavudine;
2-deoxy-3'-thia-5-fluorocytidine;
2',3'-dideoxy-guanine; and
2',3'-dideoxy-guanosine.

44. The method of claim 43 wherein said nucleoside antiviral compound is (-)-2'-deoxy-3'-thiocytidine-5'-triphosphate (3TC).

45. The method of claim 42 wherein W, X, Y, and Z are each alkanoyl; and wherein said nucleoside or nucleotide antiviral compound is selected from the group consisting of:

(+)-cis-5-fluoro-1-[2-(hydroxy-methyl)-[1,3-oxathiolan-5-yl]cytosine;
(-)-2'-deoxy-3'-thiocytidine-5'-triphosphate (3TC);
(-)-cis-5-fluoro-1-[2-(hydroxy-methyl)-[1,3-oxathiolan-5- yl]cytosine (FTC);
(-)2',3', dideoxy-3'-thiacytidine [(-)-SddC];
1-2'-deoxy-2'-fluoro-beta-D-arabinofuranosyl)-5- iodocytosine (FIAC);
1-(2'-deoxy-2'-fluoro-beta-D-arabinofuranosyl)-5-iodocytosine triphosphate (FIACTP);
1-(2'-deoxy-2'-fluoro-beta-D-arabinofuranosyl)-5-methyluarcil (FMAU);
1-beta-D-ribofuranosyl-1,2,4,-triazole-3-carboxamide;
2',3'-dideoxy-3'-fluoro-5-methyl-dexocytidine (FddMeCyt);
2',3'-dideoxy-3'-chloro-5-methyl-dexocytidine (ClddMeCyt);
2',3'-dideoxy-3'-amino-5-methyl-dexocytidine (AddMeCyt);
2',3'-dideoxy-3'-fluoro-5-methyl-cytidine (FddMeCyt);
2',3'-dideoxy-3'-chloro-5-methyl-cytidine (ClddMeCyt);
2',3'-dideoxy-3'-amino-5-methyl-cytidine (AddMeCyt);
2',3'-dideoxy-3'-fluorothymidine (FddThd);
2',3'-dideoxy-beta-L-5-fluorocytidine (beta-L-FddC);
2',3'-dideoxy-beta-L-5-thiacytidine;
2',3'-dideoxy-beta-L-5-cytidine (beta-L-ddC);
2'-deoxy-3'-thia-5-fluorocytosine;
3'-amino-5methyl-dexocytidine (AddMeCyt);
3'-azido-3'-deoxythymidine (AZT);
3'-chloro-5-methyl-dexocytidine (ClddMeCyt);
9- (2-phosphonyl-methoxyethyl)-2',6'-diaminopurine-2',3'- dideoxyriboside;
9- (2-phosphonylmethoxyethyl) adenine (PMEA);
acyclovir triphosphate (ACVTP);
D-carbocyclic-2'-deoxyguanosine (CdG);
dideoxy-cytidine;
dideoxy-cytosine (ddC);
dideoxy-guanine (ddG);
dideoxy-inosine (ddI);
E-5- (2-bromovinyl)-2'-deoxyuridine triphosphate;
fluoro-arabinofuranosyl-iodouracil;
stavudine;
2-deoxy-3'-thia-5-fluorocytidine;
2',3'-dideoxy-guanine; and
2',3'-dideoxy-guanosine.

46. The method of claim 45 wherein said nucleoside antiviral compound is (-)-2'-deoxy-3'-thiocytidine-5'-triphosphate (3TC).

47. The method of claim 46 wherein W, X, Y, and Z are each butanoyl.

48. The method of claim 42, wherein said first amount of said N-substituted-1,5-dideoxy-1,5-imino-D-glucitol compound is in the range of from about 0.1 mg to about 100 mg/kg/day, and wherein said second amount of said nucleoside or nucleotide antiviral compound, or mixture thereof, is in the range of from about 0.1 mg/person/day to about 500 mg/person/day.

49. A method of treating a hepatits virus infection in a mammal, comprising administering to said mammal a first amount of an N-substituted,-1,5-dideoxy-1,5-imino-D-glucitol compound of Formula I or a pharmaceutically acceptable salt thereof:

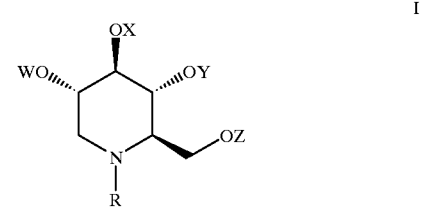

I wherein:

R is branched or straight chain alkyl having a chain length of $C_6$ to $C_{12}$; and W, X, Y, and Z are each independently selected from the group consisting of hydrogen, alkanoyl, aroyl, and trifluoroalkanoyl; and a second amount of an antiviral compound selected from the group consisting of a nucleoside antiviral compound, a nucleotide antiviral compound, and mixtures thereof;

wherein said first and second amounts of said compounds together comprise an anti-hepatitis virus effective amount of said compounds.

50. The method of claim 49 wherein said nucleoside or nucleotide antiviral compound is selected from the group consisting of:

(+)-cis-5-fluoro-1-[2-(hydroxy-methyl)-[1,3-oxathiolan-5-yl]cytosine;
(-)-2'-deoxy-3'-thiocytidine-5'-triphosphate (3TC);
(-)-cis-5-fluoro-1-[2-(hydroxy-methyl)-[1,3-oxathiolan-5-yl]cytosine (FTC);
(-)2',3', dideoxy-3'-thiacytidine [(-)-SddC];
1-2'-deoxy-2'-fluoro-beta-D-arabinofuranosyl)-5- iodocytosine (FIAC);
1-(2'-deoxy-2'-fluoro-beta-D-arabinofuranosyl)-5-iodocytosine triphosphate (FIACTP);
1-(2'-deoxy-2'-fluoro-beta-D-arabinofuranosyl)-5-methyluarcil (FMAU);
1-beta-D-ribofuranosyl-1,2,4,-triazole-3-carboxamide;
2',3'-dideoxy-3'-fluoro-5-methyl-dexocytidine (FddMeCyt);
2',3'-dideoxy-3'-chloro-5-methyl-dexocytidine (ClddMeCyt);
2',3'-dideoxy-3'-amino-5-methyl-dexocytidine (AddMeCyt);
2',3'-dideoxy-3'-fluoro-5-methyl-cytidine (FddMeCyt);
2',3'-dideoxy-3'-chloro-5-methyl-cytidine (ClddMeCyt);
2',3'-dideoxy-3'-amino-5-methyl-cytidine (AddMeCyt);
2',3'-dideoxy-3'-fluorothymidine (FddThd);
2',3'-dideoxy-beta-L-5-fluorocytidine (beta-L-FddC);
2',3'-dideoxy-beta-L-5-thiacytidine;

2',3'-dideoxy-beta-L-5-cytidine (beta-L-ddC);
2'-deoxy-3'-thia-5-fluorocytosine;
3'-amino-5methyl-dexocytidine (AddMeCyt);
3'-azido-3'-deoxythymidine (AZT);
3'-chloro-5-methyl-dexocytidine (ClddMeCyt);
9- (2-phosphonyl-methoxyethyl)-2',6'-diaminopurine-2', 3'- dideoxyriboside;
9- (2-phosphonylmethoxyethyl) adenine (PMEA);
acyclovir triphosphate (ACVTP);
D-carbocyclic-2'-deoxyguanosine (CdG);
dideoxy-cytidine;
dideoxy-cytosine (ddC);
dideoxy-guanine (ddG);
dideoxy-inosine (ddI);
E-5- (2-bromovinyl)-2'-deoxyuridine triphosphate;
fluoro-arabinofuranosyl-iodouracil;
stavudine;
2-deoxy-3'-thia-5-fluorocytidine;
2',3'-dideoxy-guanine; and
2',3'-dideoxy-guanosine.

51. The method of claim 50 wherein said nucleoside antiviral compound is (-)-2'-deoxy-3'-thiocytidine-5'- triphosphate (3TC).

52. The method of claim 49, wherein said first amount of said N-substituted-1,5-dideoxy-1,5-imino-D-glucitol compound is in the range of from about 0.1 mg to about 100 mg/kg/day, and wherein said second amount of said nucleoside or nucleotide antiviral compound, or mixture thereof, is in the range of from about 0.1 mg/person/day to about 500 mg/person/day.

53. The method of claim 52 wherein said nucleoside or nucleotied antiviral compound is selected from the group consisting of:

(+)-cis-5-fluoro-1-[2-(hydroxy-methyl)-[1,3-oxathiolan-5-yl]cytosine;

(-)-2'-deoxy-3'-thiocytidine-5'-triphosphate (3TC);

(-)-cis-5-fluoro-1-[2-(hydroxy-methyl)-[1,3-oxathiolan-5-yl]cytosine (FTC);

(-)2',3', dideoxy-3'-thiacytidine [(-)-SddC];

1-2'-deoxy-2'-fluoro-beta-D-arabinofuranosyl)-5- iodocytosine (FIAC);

1-(2'-deoxy-2'-fluoro-beta-D-arabinofuranosyl)-5-iodocytosine triphosphate (FIACTP);

1-(2'-deoxy-2'-fluoro-beta-D-arabinofuranosyl)-5-methyluarcil (FMAU);

1-beta-D-ribofuranosyl-1,2,4,-triazole-3-carboxamide;

2',3'-dideoxy-3'-fluoro-5-methyl-dexocytidine (FddMeCyt);

2',3'-dideoxy-3'-chloro-5-methyl-dexocytidine (ClddMeCyt);

2',3'-dideoxy-3'-amino-5-methyl-dexocytidine (AddMeCyt);

2',3'-dideoxy-3'-fluoro-5-methyl-cytidine (FddMeCyt);

2',3'-dideoxy-3'-chloro-5-methyl-cytidine (ClddMeCyt);

2',3'-dideoxy-3'-amino-5-methyl-cytidine (AddMeCyt);

2',3'-dideoxy-3'-fluorothymidine (FddThd);

2',3'-dideoxy-beta-L-5-fluorocytidine (beta-L-FddC);

2',3'-dideoxy-beta-L-5-thiacytidine;

2',3'-dideoxy-beta-L-5-cytidine (beta-L-ddC);

2'-deoxy-3'-thia-5-fluorocytosine;

3'-amino-5-methyl-dexocytidine (AddMeCyt);

3'-azido-3'-deoxythymidine (AZT);

3'-chloro-5-methyl-dexocytidine (ClddMeCyt);

9-(2-phosphonyl-methoxyethyl)-2',6'-diaminopurine-2', 3'- dideoxyriboside;

9-(2-phosphonylmethoxyethyl) adenine (PMEA);

acyclovir triphosphate (ACVTP);

D-carbocyclic-2'-deoxyguanosine (CdG);

dideoxy-cytidine;

dideoxy-cytosine (ddC);

dideoxy-guanine (ddG);

dideoxy-inosine (ddI);

E-5-(2-bromovinyl)-2'-deoxyuridine triphosphate;

fluoro-arabinofuranosyl-iodouracil;

stavudine;

2-deoxy-3'-thia-5-fluorocytidine;

2',3'-dideoxy-guanine; and

2',3'-dideoxy-guanosine.

54. The method of claim 49 wherein said hepatitis virus infection is a hepatitis B virus infection.

55. The method of claim 54 wherein said mammal is a human.

* * * * *